US011715356B2

(12) United States Patent
Liu et al.

(10) Patent No.: US 11,715,356 B2
(45) Date of Patent: Aug. 1, 2023

(54) SPATIAL-TEMPORAL HAPTIC STIMULATION SYSTEMS AND METHODS

(71) Applicant: Huawei Technologies Co., Ltd., Shenzhen (CN)

(72) Inventors: Fei Liu, Plano, TX (US); Jun Xu, Plano, TX (US); Tao Huang, Plano, TX (US)

(73) Assignee: Huawei Technologies Co., Ltd., Shenzhen (CN)

( * ) Notice: Subject to any disclaimer, the term of this patent is extended or adjusted under 35 U.S.C. 154(b) by 69 days.

(21) Appl. No.: 17/511,270

(22) Filed: Oct. 26, 2021

(65) Prior Publication Data

US 2022/0051533 A1 Feb. 17, 2022

Related U.S. Application Data

(63) Continuation of application No. PCT/US2019/030000, filed on Apr. 30, 2019.

(51) Int. Cl.
*H04B 3/36* (2006.01)
*G08B 6/00* (2006.01)

(52) U.S. Cl.
CPC ..................... *G08B 6/00* (2013.01)

(58) Field of Classification Search
CPC ...... G08B 6/00; A61N 1/0456; A61N 1/0476; A61N 1/36014; G06F 3/016
See application file for complete search history.

(56) References Cited

U.S. PATENT DOCUMENTS

| | | | |
|---|---|---|---|
| 8,884,927 B1* | 11/2014 | Cheatham, III | G06F 3/0436 178/19.02 |
| 2005/0173231 A1 | 8/2005 | Gonzales | |
| 2008/0246737 A1 | 10/2008 | Benali-Khoudja et al. | |
| 2014/0306812 A1 | 10/2014 | Yu et al. | |
| 2019/0212824 A1* | 7/2019 | Keller | G06K 19/07762 |
| 2019/0215289 A1* | 7/2019 | Raskar | H04L 51/224 |

FOREIGN PATENT DOCUMENTS

| | | |
|---|---|---|
| DE | 19636779 A1 | 3/1998 |
| FR | 2882881 A1 | 8/2006 |
| FR | 2882881 A1 | 9/2006 |
| JP | 2018010582 A | 1/2018 |
| WO | 9716035 A1 | 5/1997 |

OTHER PUBLICATIONS

"IEEE Standard for Low-Rate Wireless Networks ," IEEE Computer Society, IEEE Std. 802.15, 2015, 708 pages.
(Continued)

*Primary Examiner* — Toan N Pham
(74) *Attorney, Agent, or Firm* — Conley Rose, P.C.

(57) ABSTRACT

The disclosure relates to technology for haptic stimulation. A haptic interface device comprises an array comprising haptic stimulation elements configured to generate a stimulation pattern. The haptic interface device comprises a controller configured to continually propagate the stimulation pattern on a user's skin, including repeatedly eliminate a portion of a first end of the stimulation pattern and replace the eliminated portion with a new portion at a second end of the stimulation pattern.

20 Claims, 18 Drawing Sheets

(56) References Cited

OTHER PUBLICATIONS

"Part 11: Wireless LAN Medium Access Control (MAC) and Physical Layer (PHY) Specifications",IEEE Standard for Information technology—Telecommunications and information exchange between systems—Local and metropolitan area networks—Specific requirements, IEEE Computer Society, IEEE Std. 802.11, 2007, Jun. 12, 2007, 1232 pages.

Alloway, et al., "The Roles of Thought and Experience in the Understanding of Spatio-temporal Metaphors," downloaded from the Internet, http://www.sfs.uni-tuebingen.de/~mramscar/papers/2002_ramscar_spatiotemporal.pdf%20https://www.ncbi.nlm.nih.gov/pmc/articles/PMC3172596/, 2002, 6 pages.

* cited by examiner

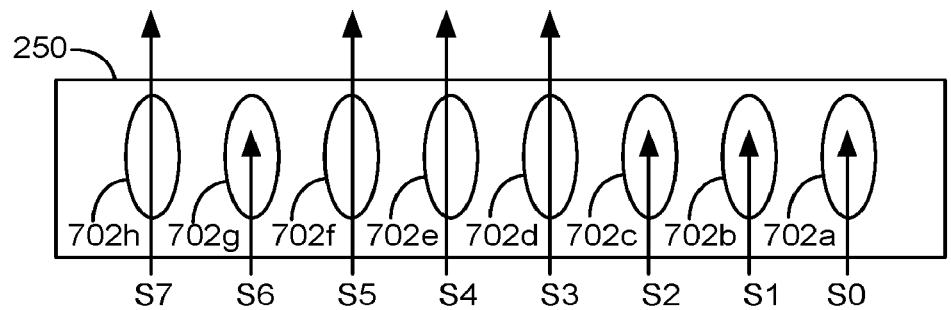
FIG. 7A
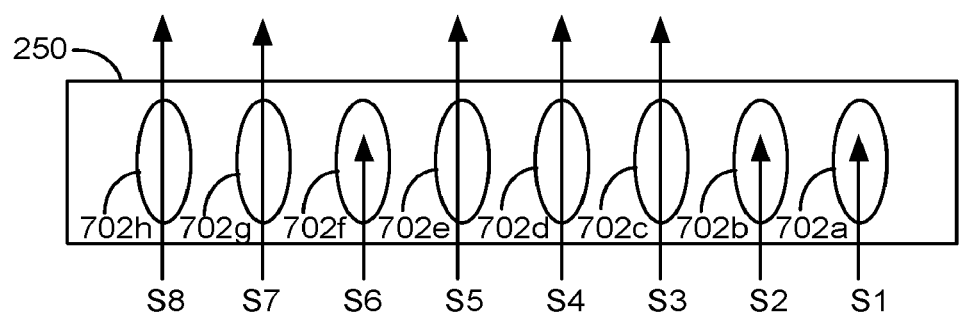
FIG. 7B  Stimulation Pattern Propagation
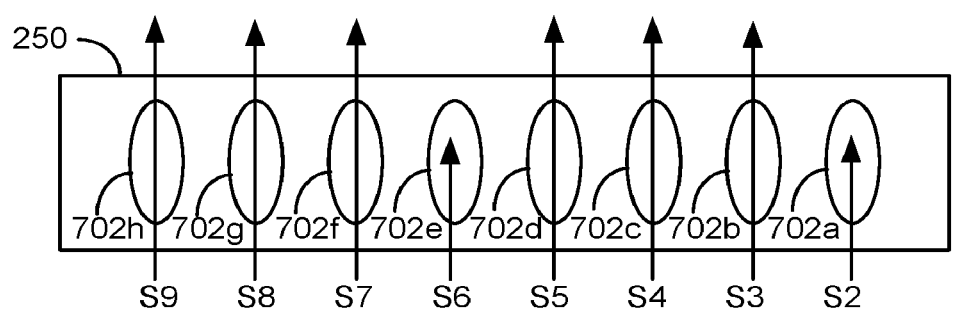
FIG. 7C  Stimulation Pattern Propagation Stimulation Pattern Propagation ←

Stimulation Pattern Propagation ←

SPATIAL-TEMPORAL HAPTIC STIMULATION SYSTEMS AND METHODS

CROSS-REFERENCE TO RELATED APPLICATIONS

This application is a continuation of International Application No. PCT/US2019/030000 filed on Apr. 30, 2019 by Futurewei Technologies, Inc., and titled "Spatial-Temporal Haptic Stimulation Systems and Methods," which is hereby incorporated by reference.

TECHNICAL FIELD

The disclosure generally relates to haptic stimulation technology.

BACKGROUND

One type of haptic stimulation, which may be referred to as a tactile stimulation, stimulates receptors in human skin. Human skin has a number of different types of receptors, which are adapted for different tactile sensations. Meissner corpuscles in the skin are adapted to sense low frequency vibrations. Merkel cells in the skin are adapted to sense pressure. Ruffini endings in the skin are adapted to sense shear deformation. Pacinian corpuscles in the skin are adapted to sense high frequency vibrations.

SUMMARY

According to one aspect of the present disclosure, there is provided a haptic stimulation device comprising a haptic interface device. The haptic interface device comprises an array comprising haptic stimulation elements configured to generate a stimulation pattern. The haptic interface device comprises a controller configured to continually propagate the stimulation pattern on a user's skin, including repeatedly eliminate a portion of a first end of the stimulation pattern and replace the eliminated portion with a new portion at a second end of the stimulation pattern. Continually propagating the stimulation pattern on a user's skin may increase a rate at which a user can consume information presented in the haptic interface device.

Optionally, in any of the preceding aspects, the controller is configured to propagate the stimulation pattern at a constant rate on the user's skin.

Optionally, in any of the preceding aspects, the array comprises rows and columns of the haptic stimulation elements. The controller is configured to propagate the stimulation pattern at the same rate for each row.

Optionally, in any of the preceding aspects, the array comprises rows and columns of the haptic stimulation elements. The controller is configured to propagate the stimulation pattern at a different rate for different rows.

Optionally, in any of the preceding aspects, the controller is configured to present two partial units of information at the same time in the stimulation pattern.

Optionally, in any of the preceding aspects, the controller is configured to present a portion of a first character and a portion of a second character in the stimulation pattern at the same time.

Optionally, in any of the preceding aspects, the controller is configured to present a portion of a first word and a portion of a second word in the stimulation pattern at the same time.

Optionally, in any of the preceding aspects, the controller is configured to move the array comprising haptic stimulation elements across the user's skin in order to propagate the stimulation pattern on the user's skin.

Optionally, in any of the preceding aspects, the array comprising haptic stimulation elements comprises a ring of haptic stimulation elements. The controller is configured to rotate the array comprising haptic stimulation elements across the user's skin in order to propagate the stimulation pattern on the user's skin.

Optionally, in any of the preceding aspects, the array comprising haptic stimulation elements comprises a straight line of haptic stimulation elements. The controller is configured to move the straight line of haptic stimulation elements across the user's skin in order to propagate the stimulation pattern on the user's skin.

Optionally, in any of the preceding aspects, the controller is configured to modify the stimulation pattern over time based on a long short-term memory model.

Optionally, in any of the preceding aspects, the controller is configured to attenuate portions of the stimulation pattern over time.

Optionally, in any of the preceding aspects, the controller is configured to represent a three-dimensional object in the array comprising haptic stimulation elements.

Optionally, in any of the preceding aspects, the controller is configured to spatially represent a first dimension and a second dimension of a three-dimensional object in the array and temporally represent a third dimension of the three-dimensional object in the array.

Optionally, in any of the preceding aspects, the controller is configured to control a rate at which the stimulation pattern propagates in different regions of the array in order to temporally represent the third dimension of the three-dimensional object.

Optionally, in any of the preceding aspects, the controller is configured to represent velocity of an object in the array comprising haptic stimulation elements by the rate at which the stimulation pattern is propagated.

According to one other aspect of the present disclosure, there is provided a method for providing a haptic stimulation interface. The method comprises generating a stimulation pattern with an array comprising haptic stimulation elements, the stimulation pattern comprising a first end and a second end. The method further comprises continually propagating the stimulation pattern on a user's skin, including repeatedly eliminating a portion of a first end of the stimulation pattern and replace the eliminated portion with a new portion at a second end of the stimulation pattern.

According to still one other aspect of the present disclosure, there is provided a haptic stimulation device comprising a haptic stimulation interface comprising an array of tactile pixels configured to stimulate receptors in skin of a user with a stimulation pattern. The stimulation pattern comprises a first end and a second end. The haptic stimulation device comprises a receiver configured to receive information to present in the haptic stimulation interface. The haptic stimulation device comprises a processor configured to continually propagate the stimulation pattern on the user's skin in order to present the information, including eliminate a portion of a first end of the stimulation pattern and replace the eliminated portion with a new portion at a second end of the stimulation pattern.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

BRIEF DESCRIPTION OF THE DRAWINGS

Aspects of the present disclosure are illustrated by way of example and are not limited by the accompanying figures for which like references indicate elements.

FIGS. 7A-7C depict a haptic stimulation interface at three points in time in order to illustrate an embodiment of propagating a stimulation pattern.

DETAILED DESCRIPTION

Figure 1:
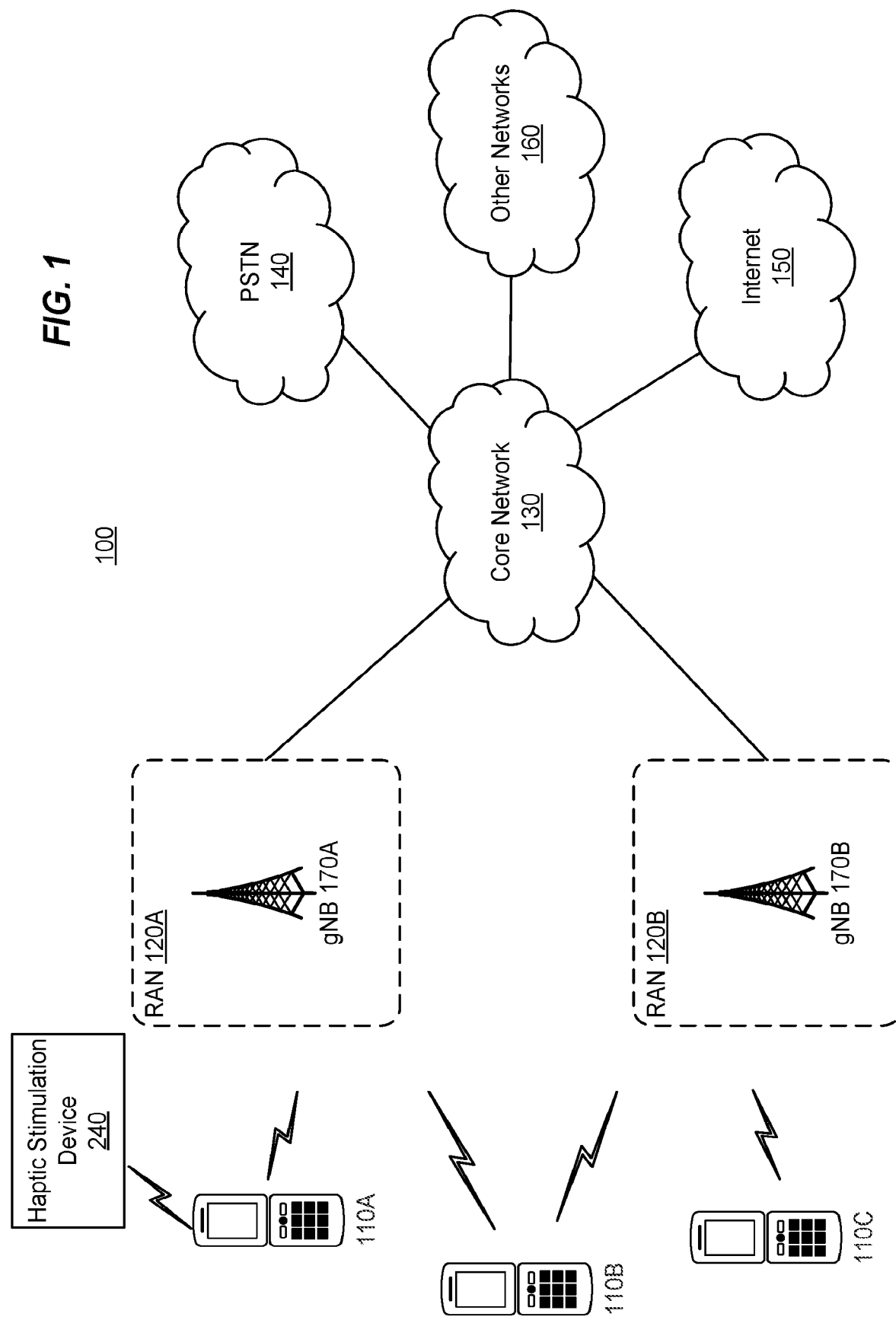
FIG. 1 illustrates a wireless network for communicating data.

The present disclosure will now be described with reference to the figures, which in general relate to haptic stimulation systems and methods. One technical challenge of providing haptic stimulation systems and methods is that oftentimes the stimulation pattern that can be generated can only present a very limited amount of information at one time. To some extent this is due to the haptic stimulation device having a relatively small number of haptic stimulation elements. Each haptic stimulation element may be referred to as a "tactile pixel" or a "tixel." The limited number of tixels is in contrast to interfaces such as electronic visual displays, which may contain an enormous number of visual display elements (e.g., pixels). Thus, an electronic visual display might be used to simultaneously present a large number of words or a complex image. In contrast, a haptic stimulation device might display a single character (e.g., letter of an alphabet) or perhaps a few characters at one time. A consequence of the foregoing is that it can take a user much longer to consume information that is presented in a haptic stimulation device than in an electronic visual display. Techniques disclosed herein increase the rate at which a user can consume information presented in a haptic stimulation device. This not only saves the user's time, but can reduce power consumption. If the haptic stimulation device is battery powered, techniques disclosed herein can extend battery life. Therefore, regardless of the source of power, the haptic stimulation device operates more efficiently.

A haptic stimulation device has an array comprising haptic stimulation elements configured to generate a stimulation pattern, in some embodiments. The haptic interface device has a controller configured to continually propagate the stimulation pattern on a user's skin, in some embodiments. The term "continually" as used herein includes either without interruption or repeatedly at regular intervals. The phrase "continually propagate a stimulation pattern" as used herein means to propagate the stimulation pattern either without interruption or repeatedly at regular intervals. Continually propagating the stimulation pattern on the user's skin can speed the rate at which the user is able to consume information. For example, a user may be able to read Braille or alphabetical characters faster due to the continual propagation of the stimulation pattern. In some embodiments, rather than displaying one character at a time, the controller propagates (or scrolls) through characters, such that when a portion of one character is leaving the stimulation pattern a new character is entering the stimulation pattern. Thus, the stimulation pattern might contain portions of two different characters at the same time. That "partial information" by itself might be difficult to comprehend. However, the user has the benefit of having already consumed the first character when the second character is starting to be presented. The user can remember the first character even though it is only partially displayed (or not displayed at all). Moreover, the user may be able to anticipate the next character. Hence, even with only partial information about the next character, the user may be able to start to determine what the next character is. Hence, the speed at which the user is able to identify the next character may increase, which increases the overall speed of consuming information.

In some embodiments, when the controller propagates the stimulation pattern, the controller uses both spatial and temporal variations to convey information in the stimulation pattern. In one embodiment, the controller describes a three-dimensional (3D) object in the stimulation pattern. For example, the array comprising haptic stimulation elements may be a two-dimensional array, that is used to present a first dimension and a second dimension of the 3D object. The third dimension of the 3D object is described using temporal variations, in one embodiment. For example, the rate at which the controller propagates different regions of the stimulation pattern can be used to convey the third dimension.

It is understood that the present embodiments of the disclosure may be implemented in many different forms and that claims scopes should not be construed as being limited to the embodiments set forth herein. Rather, these embodiments are provided so that this disclosure will be thorough and complete and will fully convey the inventive embodiment concepts to those skilled in the art. Indeed, the disclosure is intended to cover alternatives, modifications and equivalents of these embodiments, which are included within the scope and spirit of the disclosure as defined by the appended claims. Furthermore, in the following detailed description of the present embodiments of the disclosure, numerous specific details are set forth in order to provide a thorough understanding. However, it will be clear to those of ordinary skill in the art that the present embodiments of the disclosure may be practiced without such specific details.

FIG. 1 illustrates a wireless network for communicating data. The communication system 100 includes, for example, user equipment 110A, 110B, and 110C, radio access networks (RANs) 120A and 120B, a core network 130, a public switched telephone network (PSTN) 140, the Internet 150, and other networks 160. Additional or alternative networks include private and public data-packet networks including corporate intranets. While certain numbers of these components or elements are shown in the figure, any number of these components or elements may be included in the system 100.

In one embodiment, the wireless network may be a fifth generation (5G) network including at least one 5G base station which employs orthogonal frequency-division multiplexing (OFDM) and/or non-OFDM and a transmission time interval (TTI) shorter than 1 ms (e.g., 100 or 200 microseconds), to communicate with the communication devices. In general, a base station may also be used to refer to any of the eNB and the 5G BS (gNB). In addition, the network may further include a network server for processing information received from the communication devices via the at least one eNB or gNB.

System 100 enables multiple wireless users to transmit and receive data and other content. The system 100 may implement one or more channel access methods, such as but not limited to code division multiple access (CDMA), time division multiple access (TDMA), frequency division multiple access (FDMA), orthogonal FDMA (OFDMA), or single-carrier FDMA (SC-FDMA).

The user equipment (UE) 110A, 110B, and 110C, which can be referred to individually as a UE 110, or collectively as the UEs 110, are configured to operate and/or communicate in the system 100. For example, a UE 110 can be configured to transmit and/or receive wireless signals or wired signals. Each UE 110 represents any suitable end user device and may include such devices (or may be referred to) as a user equipment/device, wireless transmit/receive unit (UE), mobile station, fixed or mobile subscriber unit, pager, cellular telephone, personal digital assistant (PDA), smartphone, laptop, computer, touchpad, wireless sensor, wearable devices or consumer electronics device.

In the depicted embodiment, the RANs 120A, 120B include one or more base stations (BSs) 170A, 170B, respectively. The RANs 120A and 120B can be referred to individually as a RAN 120, or collectively as the RANs 120. Similarly, the base stations (BSs) 170A and 170B can be referred to individually as a base station (BS) 170, or collectively as the base stations (BSs) 170. Each of the BSs 170 is configured to wirelessly interface with one or more of the UEs 110 to enable access to the core network 130, the PSTN 140, the Internet 150, and/or the other networks 160. For example, the base stations (BSs) 170 may include one or more of several well-known devices, such as a base transceiver station (BTS), a Node-B (NodeB), an evolved NodeB (eNB), a next (fifth) generation (5G) NodeB (gNB), a Home NodeB, a Home eNodeB, a site controller, an access point (AP), or a wireless router, or a server, router, switch, or other processing entity with a wired or wireless network.

In one embodiment, the BS 170A forms part of the RAN 120A, which may include one or more other BSs 170, elements, and/or devices. Similarly, the BS 170B forms part of the RAN 120B, which may include one or more other BSs 170, elements, and/or devices. Each of the BSs 170 operates to transmit and/or receive wireless signals within a particular geographic region or area, sometimes referred to as a "cell." In some embodiments, multiple-input multiple-output (MIMO) technology may be employed having multiple transceivers for each cell.

The BSs 170 communicate with one or more of the UEs 110 over one or more air interfaces (not shown) using wireless communication links. The air interfaces may utilize any suitable radio access technology.

It is contemplated that the system 100 may use multiple channel access functionality, including for example schemes in which the BSs 170 and UEs 110 are configured to implement the Long Term Evolution wireless communication standard (LTE), LTE Advanced (LTE-A), and/or LTE Multimedia Broadcast Multicast Service (MBMS). In other embodiments, the base stations 170 and user equipment 110A-110C are configured to implement UMTS, HSPA, or HSPA+ standards and protocols. Of course, other multiple access schemes and wireless protocols may be utilized.

The RANs 120 are in communication with the core network 130 to provide the UEs 110 with voice, data, application, Voice over Internet Protocol (VoIP), or other services. As appreciated, the RANs 120 and/or the core network 130 may be in direct or indirect communication with one or more other RANs (not shown). The core network 130 may also serve as a gateway access for other networks (such as PSTN 140, Internet 150, and other networks 160). In addition, some or all of the UEs 110 may include functionality for communicating with different wireless networks over different wireless links using different wireless technologies and/or protocols.

The RANs 120 may also include millimeter and/or microwave access points (APs).

The APs may be part of the BSs 170 or may be located remote from the BSs 170. The APs may include, but are not limited to, a connection point (an mmW CP) or a BS 170 capable of mmW communication (e.g., a mmW base station). The mmW APs may transmit and receive signals in a frequency range, for example, from 24 gigahertz (GHz) to 100 GHz, but are not required to operate throughout this range. As used herein, the term base station is used to refer to a base station and/or a wireless access point.

Although FIG. 1 illustrates one example of a communication system, various changes may be made to FIG. 1. For example, the communication system 100 could include any number of user equipment, base stations, networks, or other components in any suitable configuration. It is also appreciated that the term user equipment may refer to any type of wireless device communicating with a radio network node in a cellular or mobile communication system. Non-limiting examples of user equipment are a target device, device-to-device (D2D) user equipment, machine type user equipment or user equipment capable of machine-to-machine (M2M) communication, laptops, PDA, iPad, Tablet, mobile terminals, smart phones, laptop embedded equipped (LEE), laptop mounted equipment (LME) and USB dongles.

In one embodiment, a UE 110 has a wireless connection to a haptic stimulation device 240. The UE 110 sends information (e.g., digital data) to the haptic stimulation device 240 over the wireless connection, in one embodiment. The information is presented in haptic stimulation interface 250. In one embodiment, a haptic stimulation system comprises the haptic stimulation device 240 but does not include the UE 110.

Figure 2:
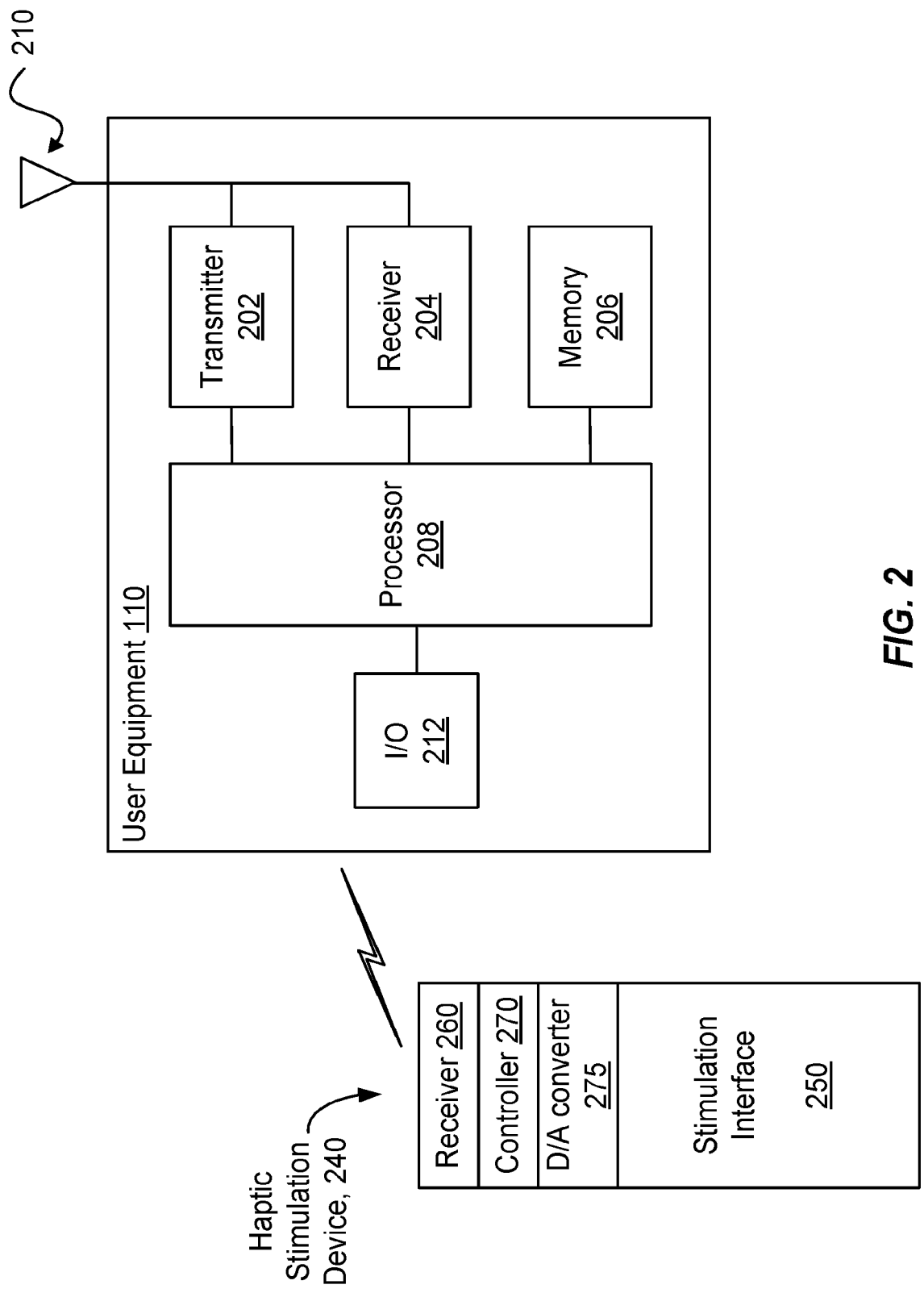
FIG. 2 illustrates one embodiment of a haptic stimulation system.

FIG. 2 illustrates one embodiment of a haptic stimulation system. The haptic stimulation system comprises a haptic stimulation device 240 and the UE 110, in this embodiment. The haptic stimulation system comprises the haptic stimulation device 240 but does not include the UE 110, in another embodiment. The UE 110 may for example be a mobile telephone, but may be other devices in further examples such as a desktop computer, laptop computer, tablet, handheld computing device, automobile computing device and/or other computing devices. As shown in the figure, the exemplary UE 110 is shown as including at least one transmitter 202, at least one receiver 204, memory 206, at least one processor 208, and at least one input/output (I/O) device 212. The processor 208 can implement various processing operations of the UE 110. For example, the processor 208 can perform signal coding, data processing, power control, input/output processing, or any other functionality enabling the UE 110 to operate in the system 100 (FIG. 1). The processor 208 may include any suitable processing or computing device configured to perform one or more operations. For example, the processor 208 may include a microprocessor, microcontroller, digital signal processor, field programmable gate array, or application specific integrated circuit. The memory 206 is non-transitory memory storage, in one embodiment. The memory 206 is a non-transitory computer readable medium, in one embodiment.

The transmitter 202 can be configured to modulate data or other content for transmission by at least one antenna 210. The transmitter 202 can also be configured to amplify, filter and a frequency convert RF signals before such signals are provided to the antenna 210 for transmission. The transmitter 202 can include any suitable structure for generating signals for wireless transmission.

The receiver 204 can be configured to demodulate data or other content received by the at least one antenna 210. The receiver 204 can also be configured to amplify, filter and frequency convert RF signals received via the antenna 210. The receiver 204 is an RF signal receiver, in some embodiments. The receiver 204 can include any suitable structure for processing signals received wirelessly. The antenna 210 can include any suitable structure for transmitting and/or receiving wireless signals. The same antenna 210 can be used for both transmitting and receiving RF signals, or alternatively, different antennas 210 can be used for transmitting signals and receiving signals.

It is appreciated that one or multiple transmitters 202 could be used in the UE 110, one or multiple receivers 204 could be used in the UE 110, and one or multiple antennas 210 could be used in the UE 110. Although shown as separate blocks or components, at least one transmitter 202 and at least one receiver 204 could be combined into a transceiver. Accordingly, rather than showing a separate block for the transmitter 202 and a separate block for the receiver 204 in FIG. 2, a single block for a transceiver could have been shown. At least one of the transmitters 202 is configured to communication with the haptic stimulation device 240, in one embodiment. At least one of the receivers 204 is configured to communication with the haptic stimulation device 240, in one embodiment. Such a transmitter and/or receiver comprises a wireless communication interface configured to communicate with the haptic stimulation device 240, in one embodiment.

The UE 110 further includes one or more input/output devices 212. The input/output devices 212 facilitate interaction with a user. Each input/output device 212 includes any suitable structure for providing information to or receiving information from a user, such as a speaker, microphone, keypad, keyboard, display, or touch screen. Note that some users may have a difficult time using one or more of the structures for receiving information. For example, some users may have a difficult time seeing or reading a visual display on the UE 110. As another example, some users may have a difficult time hearing a speaker on the UE 110. Embodiments of a haptic stimulation device 240 allow a user to obtain such information from the UE 110.

In addition, the UE 110 includes at least one memory 206. The memory 206 stores instructions and data used, generated, or collected by the UE 110. For example, the memory 206 could store software or firmware instructions executed by the processor(s) 208 and data used to reduce or eliminate interference in incoming signals. Each memory 206 includes any suitable volatile and/or non-volatile storage and retrieval device(s). Any suitable type of memory may be used, such as random access memory (RAM), read only memory (ROM), hard disk, optical disc, subscriber identity module (SIM) card, memory stick, secure digital (SD) memory card, and the like.

The UE 110 has a wireless connection to the haptic stimulation device 240. The haptic stimulation device 240 has a haptic stimulation interface 250 (also referred to more briefly as a "stimulation interface"), a receiver 260, a controller 270, and a digital-to-analog (D/A) converter 275. The receiver 260 may comprise a wireless receiver configured to communicate wirelessly with the UE 110. The receiver 260 may be configured to communicate using a variety of wireless communication protocols including, but not limited to, an IEEE (Institute of Electrical and Electronics Engineers) 802.11 protocol or an IEEE 802.15 protocol. In one embodiment, the receiver 260 is configured to communicate using Bluetooth®. Optionally, the haptic stimulation device 240 may have a transmitter, which may be configured to communicate using a variety of wireless communication protocols. In one embodiment, the user is allowed to select what information gets transferred from the UE 110 to the haptic stimulation device 240. As the user becomes more comfortable with the haptic stimulation device 240 the user might request that more detailed information be sent. For example, the user might select to have a notification that an email has been received, key words from the email, the entire email, etc.

The stimulation interface 250 is configured to generate a haptic stimulation pattern. When a user's skin is in contact with the stimulation interface 250, the haptic stimulation pattern stimulates receptors in the user's skin, in one embodiment. The receptors may include, but are not limited to, Meissner corpuscles, Merkel cells, Ruffini endings, and Pacinian corpuscles. The stimulation interface 250 is not required to stimulate all of these types of receptors. In one embodiment, the stimulation interface 250 stimulates a subset of one or more types of receptors (e.g., Meissner corpuscles, Merkel cells, Ruffini endings, and/or Pacinian corpuscles). The stimulation interface 250 has a set (e.g., pattern, array, etc.) of stimulation elements, in one embodiment. The stimulation interface 250 uses mechanical motion (e.g., mechanical vibration) in order to stimulate receptors in human skin, in some embodiments. The stimulation elements each comprise an electroacoustic transducer configured to generate an acoustic wave, in one embodiment.

The controller 270 is configured to control operations of the haptic stimulation device 240. The controller 270 is configured to control transfer of data from the UE 110 by way of the receiver 260, in one embodiment. Data transfer is unidirectional, from the UE 110 to the haptic stimulation device 240, in one embodiment. Data transfer is bi-directional, in one embodiment. Therefore, the haptic stimulation device 240 may report configuration information, status, etc. to the UE 110.

The controller 270 is configured to control the presentation of the data in the stimulation interface 250, in one embodiment. The controller 270 is configured to continually propagate a stimulation pattern on a user's skin, in one embodiment. The D/A converter 275 is configured to convert a digital signal to an analog signal. In one embodiment, the controller 270 processes a first digital signal from the UE 110 and provides a second digital signal to the D/A converter 275. Based on the second digital signal from the controller 270, the D/A converter 275 outputs an analog signal to drive the stimulation interface 250. The first and second digital signals may be different as the controller 270 may handle functions such as generating a suitable digital signal for the configuration of the stimulation interface 250. In one embodiment, the UE 110 handles these functions, wherein the first and second digital signals may be the same.

The controller 270 may be implemented in hardware, software, or a combination of hardware and software. Hardware control circuit components for implementing the controller 270 may include, but are not limited to, Field-programmable Gate Arrays (FPGAs), Application-specific Integrated Circuits (ASICs), Application-specific Standard Products (ASSPs), System-on-a-chip systems (SOCs), Complex Programmable Control Circuit Devices (CPLDs), special purpose computers, etc. In one embodiment, the controller 270 is implemented with software (stored on a storage device) used to program one or more processors. Thus, the controller 270 may comprise a storage device and a processor.

The controller 270 works together with the UE 110 to present information in the stimulation interface 250, in one embodiment. For example, by executing instructions stored in the memory 206 on the processor 208, the UE 110 may send digital data to the receiver 260. Thus, in one embodiment, the combination of the controller 270, processor 208, and memory 206 may be referred to as a control circuit configured to present information in the haptic stimulation interface 250.

Figure 3:
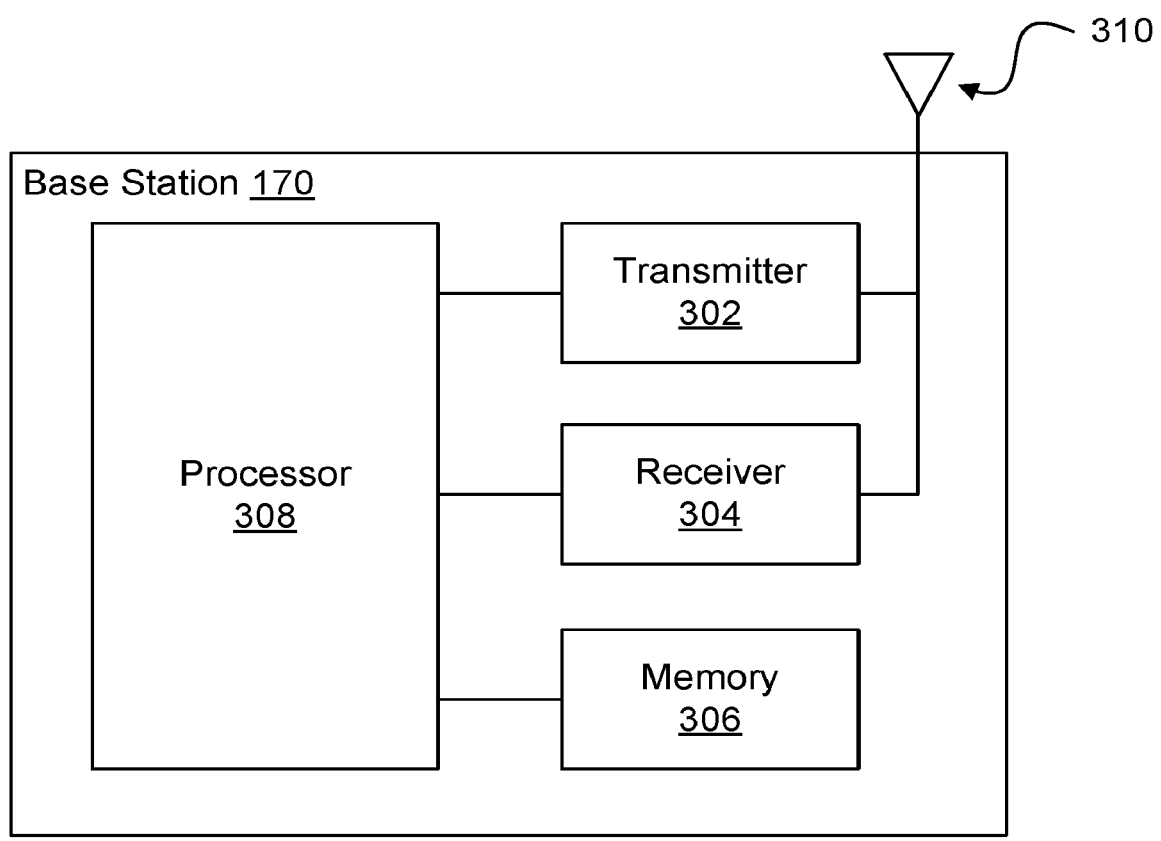
FIG. 3 illustrates an example Base Station.

FIG. 3 illustrates an example BS 170 that may implement the methods and teachings according to this disclosure. As shown in the figure, the BS 170 includes at least one processor 308, at least one transmitter 302, at least one receiver 304, one or more antennas 310, and at least one memory 306. The processor 308 implements various processing operations of the BS 170, such as signal coding, data processing, power control, input/output processing, or any other functionality. Each processor 308 includes any suitable processing or computing device configured to perform one or more operations. Each processor 308 could, for example, include a microprocessor, microcontroller, digital signal processor, field programmable gate array, or application specific integrated circuit. The memory 306 is non-transitory memory storage, in one embodiment.

Each transmitter 302 includes any suitable structure for generating signals for wireless transmission to one or more UEs 110 or other devices. Each receiver 304 includes any suitable structure for processing signals received wirelessly from one or more UEs 110 or other devices. Although shown as separate blocks or components, at least one transmitter 302 and at least one receiver 304 could be combined into a transceiver. Each antenna 310 includes any suitable structure for transmitting and/or receiving wireless signals. While a common antenna 310 is shown here as being coupled to both the transmitter 302 and the receiver 304, one or more antennas 310 could be coupled to the transmitter(s) 302, and one or more separate antennas 310 could be coupled to the receiver(s) 304. Each memory 306 includes any suitable volatile and/or non-volatile storage and retrieval device(s).

Figure 4:
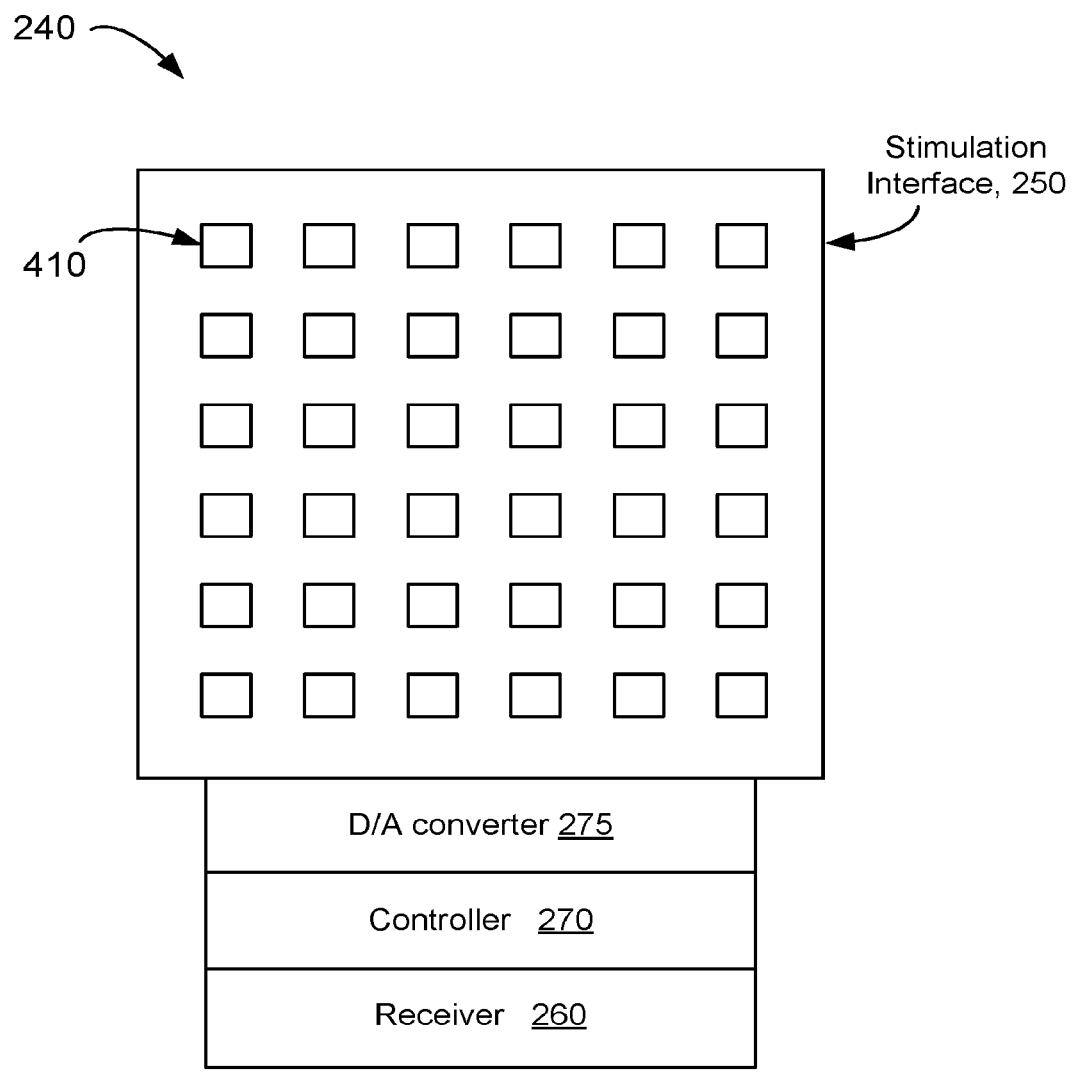
FIG. 4 depicts one embodiment of a haptic stimulation device.

FIG. 4 depicts one embodiment of a haptic stimulation device 240. The stimulation interface 250 has an array comprising haptic stimulation elements 410 (also referred to more briefly as "stimulation elements"). Each haptic stimulation element 410 may also be referred to herein as a "tactile pixel" or a "tixel." The array of stimulation elements 410 are used to stimulate receptors (e.g., Meissner corpuscles, Merkel cells, Ruffini endings, and/or Pacinian corpuscles) in human skin, in one embodiment. Each stimulation element 410 may be independently controlled, in one embodiment. The set in FIG. 4 is just one example, but many other configurations of the stimulation elements 410 is possible. In this example, there is a six by six set of stimulation elements 410, for a total of 36 stimulation elements 410. The number of stimulation elements 410 can vary with implementation. There are six rows of stimulation elements 410 and six columns of stimulation elements 410 in the example in FIG. 4. It is not required that number of rows is equal to the number of rows. The stimulation elements 410 are spaced apart equally in the example in FIG. 4; however, equal spacing is not required. It is not required that the pattern be arranged in rows and columns. In one embodiment, the set comprises an array of stimulation elements 410. The term "array" is being used to refer to a systematic arrangement of similar objects such as stimulation elements 410.

The cross-sectional shape of each stimulation element 410 is depicted as a square in FIG. 4, but the stimulation elements 410 may have other cross-sectional shapes.

In one embodiment, each stimulation element 410 comprises an electrode, which may be biased to a desired voltage. Thus, the stimulation interface 250 comprises an array of electrodes configured to stimulate receptors in the user's skin, in one embodiment. In one embodiment, some of the stimulation elements 410 are referred to as activation electrodes, and other stimulation elements 410 are referred to as ground electrodes. There are one or more ground electrodes, in one embodiment. By biasing an activation electrode to a suitable voltage with the ground electrode(s) at a common voltage, a current may be made to flow through the user's skin from the activation electrode to one or more ground electrodes. The current that flows through the user's skin may be an ionic current. An activation electrode may be biased to the common voltage, in one embodiment, if it is desired to not activate that particular activation electrode.

In one embodiment, each stimulation element 410 comprises an electromechanical transducer. Thus, the stimulation interface 250 comprises an array of electromechanical transducers configured to stimulate receptors in the user's skin, in one embodiment. An electromechanical transducer is capable of converting electrical energy into mechanical energy. The mechanical energy may be in the form of mechanical vibration. For example, an electromechanical transducer may be controlled by an electrical signal (e.g., current or voltage) to cause mechanical vibration of the stimulation element 410. A pattern of stimulation elements 410 comprising electromechanical transducers is used to stimulate receptors in human skin by mechanical vibration of the electromechanical transducers, in one embodiment.

In one embodiment, each stimulation element 410 comprises an electroacoustic transducer. Thus, the stimulation interface 250 comprises an array of electroacoustic transducers configured to stimulate receptors in the user's skin, in one embodiment. An electroacoustic transducer is capable of converting electrical energy into acoustic energy. The acoustic energy may be in the form of a sound wave. For example, an electroacoustic transducer may be controlled by an electrical signal (e.g., current or voltage) to generate a sound wave. In one embodiment, each electroacoustic transducer comprises an audio speaker. An array of stimulation elements 410 comprising electroacoustic transducers is used to stimulate receptors in human skin by mechanical vibration of the electroacoustic transducers, in one embodiment.

An electroacoustic transducer could be between about 0.5 mm to 2 mm in diameter. However, electroacoustic transducers smaller than 0.5 mm or larger than 2 mm may also be used for stimulation elements 410. In some embodiments, the electroacoustic transducers are driven to create sound waves that are inaudible to a human ear. In one embodiment, the electroacoustic transducers are driven to create sound waves having a frequency below 20 Hertz (Hz). In some embodiments, the electroacoustic transducers are driven to create sound waves in a frequency range between 10 Hz to 10 kilohertz (kHz). However, the electroacoustic transducers could be driven to create sound waves below 10 Hz or greater than 10 kHz.

In one embodiment, the electroacoustic transducers are driven to create sound waves having a sound pressure level at one meter from the stimulation interface 250 of less than 40 decibel (dB). However, the electroacoustic transducers could be driven to create sound waves having a sound pressure level at one meter from the stimulation interface 250 of greater than 40 dB, in some embodiments. In one embodiment, the electroacoustic transducers are driven to create sound waves having an amplitude between 0 dB to 40 dB at a distance of one meter from the stimulation interface 250.

In one embodiment, each stimulation element 410 comprises an electrothermal transducer. Thus, the stimulation interface 250 comprises an array of electrothermal transducers configured to stimulate receptors in the user's skin, in one embodiment. An electrothermal transducer is capable of converting electrical energy into thermal energy. For example, an electrothermal transducer may be controlled by an electrical signal (e.g., current or voltage) to generate thermal energy. In one embodiment, each electrothermal transducer comprises a resistor. In one embodiment, each electrothermal transducer comprises a diode. An array of stimulation elements 410 comprising electrothermal transducers is used to stimulate receptors in human skin by relative temperature of the electrothermal transducers, in one embodiment.

In one embodiment, a single stimulation element 410 by itself may stimulate receptors in the human skin. For example, each stimulation element may comprise an electromechanical transducer that is controlled by an electrical signal (e.g., current or voltage) to generate mechanical vibration. In one embodiment, two or more stimulation elements 410 work together to stimulate receptors in the human skin. For example, each stimulation element may comprise an electrode such that a current flows from the point of contact of the user's skin with an activation electrode, through the user's skin, and to a point of contact of the user's skin with a ground electrode. Note that the current being referred to within the user's skin is ionic current, in one embodiment.

The format of the information provided by the UE 110 to the haptic stimulation device 240 may vary depending on the implementation. For example, the information may be "raw data," such as text data or even image data. In this case, the haptic stimulation device 240 is configured to determine how to map the "raw data" to the pattern of haptic stimulation elements 410. However, the UE 110 may provide the information in a more refined format. For example, the UE 110 may have knowledge of the configuration of the pattern of stimulation elements 410. In this case, the UE 110 may instruct the haptic stimulation device 240 what should be presented in each of the stimulation elements 410.

Figure 5:
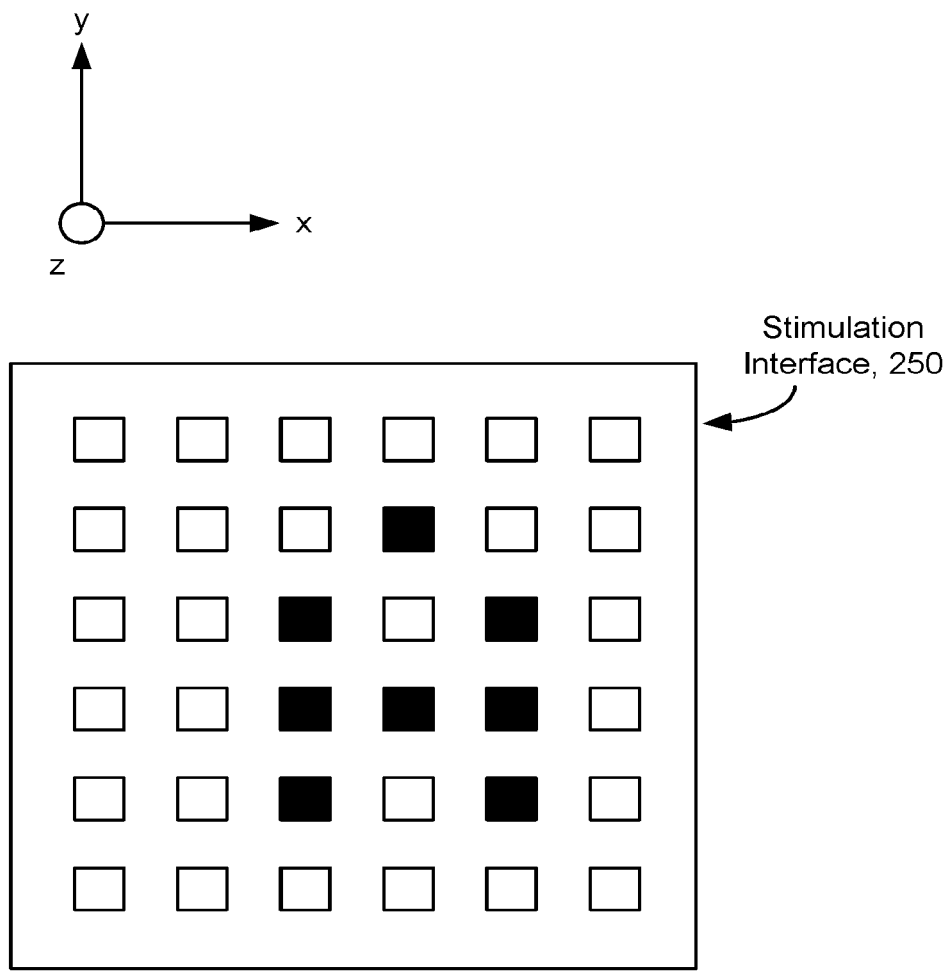
FIG. 5 depicts an embodiment of presenting information in a haptic stimulation interface in a presentation mode referred to herein as "symbolic representations of letters."

FIG. 5 depicts an embodiment of presenting information in a haptic stimulation interface 250 in a presentation mode referred to herein as "symbolic representations of letters." The letter "A" from the English alphabet is being represented on the haptic stimulation interface 250. In this example, the representation in the haptic stimulation interface 250 has a visual appearance of the letter "A" from the English alphabet. This concept may be applied to alphabets of other languages.

Figure 6:
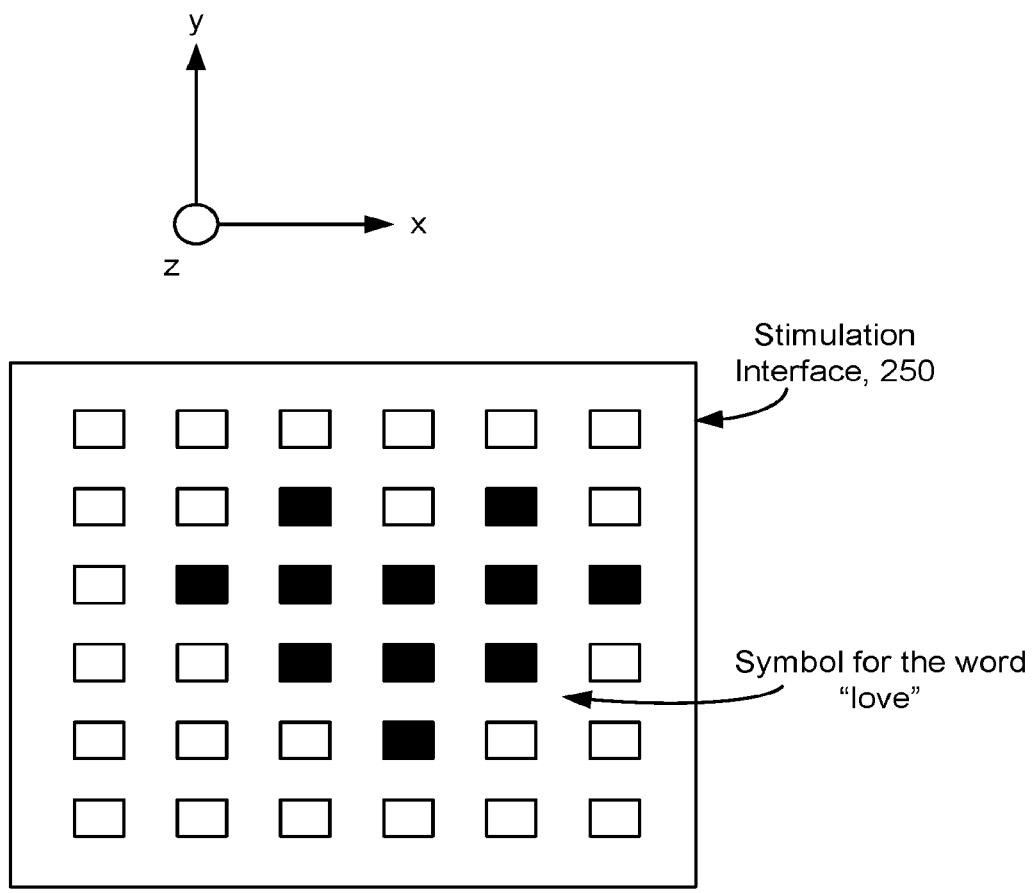
FIG. 6 depicts an embodiment of presenting information in a haptic stimulation interface in a presentation mode referred to herein as "symbolic representations of words."

FIG. 6 depicts an embodiment of presenting information in a haptic stimulation interface 250 in a presentation mode referred to herein as "symbolic representations of words." The word "love" from the English alphabet is being represented on the haptic stimulation interface 250. In this example, the representation in the haptic stimulation interface 250 has a visual appearance of the symbol of a heart, which in this example is a symbolic representation of the word "love." Note that being able to present an entire word, as opposed to a single letter, in the haptic stimulation interface 250 allows haptic stimulation interface 250 to be more efficient at presenting information to the user. For example, it can take far less time to present an email to the user. However, in some cases, the user is unable to interpret the more complex words. In other words, the user may be better able to interpret letters of an alphabet.

The concepts of FIGS. 5 and 6 may be applied to characters or symbols for writing in other languages. Thus, one embodiment comprises a presentation mode referred to herein as a "symbolic representation of characters for writing in a language." For example, in one embodiment, the presentation mode is symbolic representations of Chinese characters. Here, Chinese characters refers to any of the known characters that have been developed to write a Chinese language. In one embodiment, Braille characters are presented in the stimulation interface 250.

FIGS. 7A-7C depict a haptic stimulation interface 250 at three points in time in order to illustrate an embodiment of propagating a stimulation pattern. The stimulation pattern is propagated on a user's skin, in some embodiment. The user's skin is not expressly depicted in FIGS. 7A-7C. FIG. 7A depicts a haptic stimulation interface 250 having eight haptic stimulation elements (or tactile pixels) 702a-702h. FIG. 7A depicts a first point in time. The tactile pixels 702a-702h may be referred to as an array of tactile pixels. In this example, the arrow has a single row. The array has multiple rows, in some embodiments. FIG. 4 depicts an example in which the array has multiple rows. Referring again to FIG. 7A, tactile pixel 702a may be referred to as a first end of the array, and tactile pixel 702h may be referred to as a second end of the array.

Tactile pixels 702a-702h are respectively presenting signal elements S0-S7. Collectively, the signal elements may be referred to as a stimulation pattern (or signal) being presented in the haptic stimulation interface 250. For example, tactile pixel 702a is presenting signal element S0, tactile pixel 702b is presenting signal element S1, etc. Each signal element is represented by an arrow. The length of the arrow may represent the magnitude of the signal element. In FIGS. 7A-7C, only two different lengths are depicted for the arrows to indicate that each tactile pixel may be in one of two states, in this example. However, the tactile pixels are not required to have binary states. The pattern of signal elements may be referred to as a stimulation pattern. The pattern at a point in time may be referred to as a state of the stimulation pattern. When one or more signals change, the state of the stimulation pattern may be said to change to a new (or next) state. The states follow each other at regular intervals, in some embodiments. The stimulation pattern has a first end given by S0 and a second end given by S7, at this point in time. As will be discussed below, the stimulation pattern changes over time.

FIG. 7B depicts a second point in time that follows the first point in time. FIG. 7B depicts the immediate next state of the haptic stimulation interface 250 after the state depicted in FIG. 7A, in one embodiment. The haptic stimulation interface 250 now displays signal elements S1-S8. Thus, the stimulation pattern now comprises signal elements S1-S8. Note that signal element S0 (at the first end of the stimulation pattern) has been eliminated and a new portion to the stimulation pattern (S8) has been added to the second end of the stimulation pattern. The stimulation pattern is shown as propagating in the direction from tactile pixel 702h to tactile pixel 702a (as indicated by the arrow below "Stimulation Pattern Propagation").

FIG. 7C depicts a third point in time that follows the second point in time. FIG. 7C depicts the immediate next state of the haptic stimulation interface 250 after the state depicted in FIG. 7B, in one embodiment. The haptic stimulation interface 250 now displays signal elements S2-S9. Thus, the stimulation pattern now comprises signal elements S2-S9. Note that signal element S1 (at the first end of the stimulation pattern) has been eliminated and a new portion to the stimulation pattern (S9) has been added to the second end of the stimulation pattern. Again, the stimulation pattern is shown as propagating in the direction from tactile pixel 702h to tactile pixel 702a (as indicated by the arrow below "Stimulation Pattern Propagation").

As mentioned, the array could have multiple rows. In one embodiment, each row is treated as just described for the single row in FIGS. 7A-7C. The content of the stimulation pattern is not required to be the same for each row.

Figure 8A:
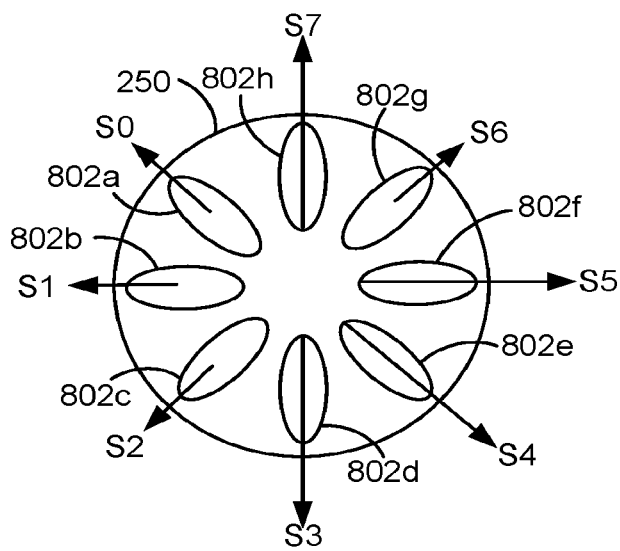
FIGS. 8A-8C depict an embodiment of a haptic stimulation interface having eight haptic stimulation elements (or tactile pixels).
Figure 8B:
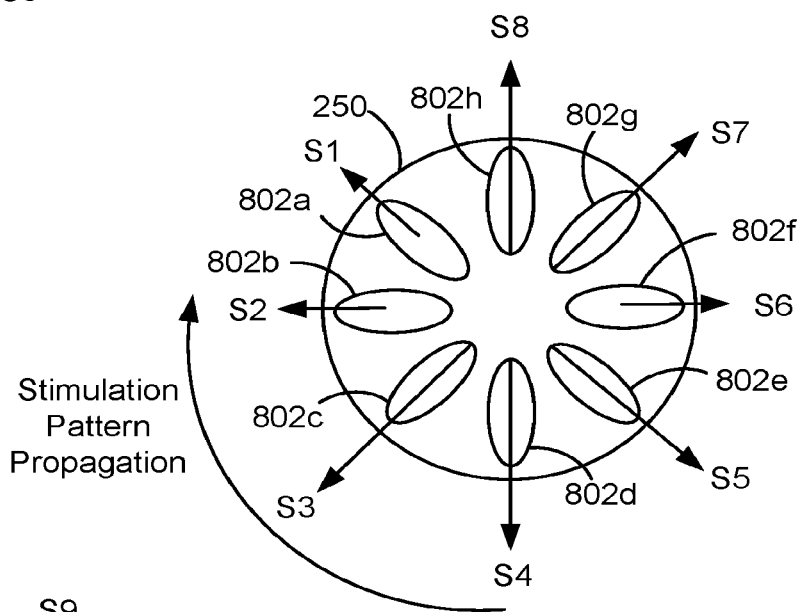
Figure 8C:
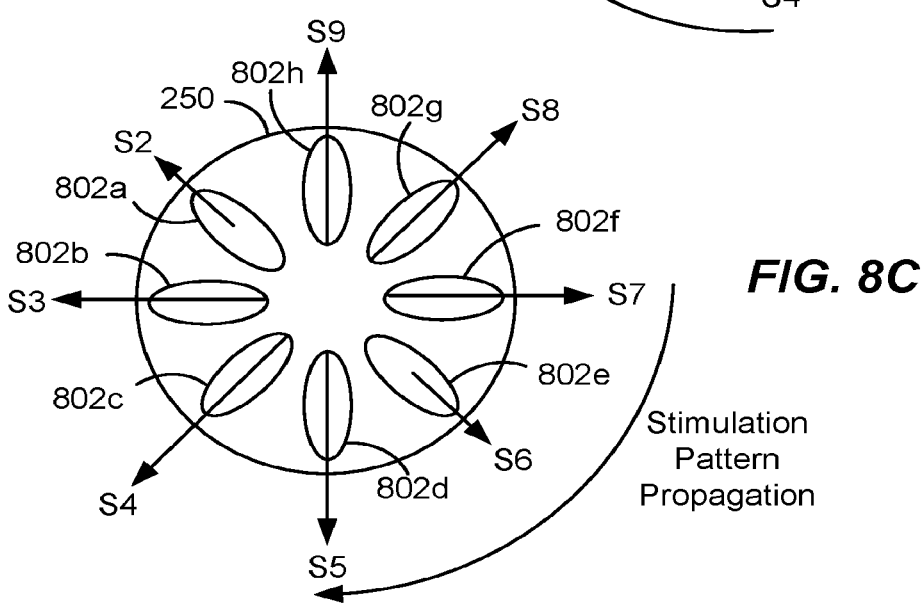

FIGS. 8A-8C depict a haptic stimulation interface 250 at three points in time in order to illustrate an embodiment of propagating a stimulation pattern. The stimulation pattern is propagated on a user's skin, in some embodiment. The user's skin is not expressly depicted in FIGS. 8A-8C. The example signal and its propagation is similar to the example of FIGS. 7A-7C. However, haptic stimulation interface 250 has what may be referred to as a circular configuration in FIGS. 8A-8C, as opposed to the straight-line configuration of FIGS. 7A-7C. FIGS. 8A-8C depict three different states of the stimulation pattern. The three states occur sequentially at regular intervals, in some embodiments.

FIG. 8A depicts an embodiment of a haptic stimulation interface 250 having eight haptic stimulation elements (or tactile pixels) 802a-802h. FIG. 8A depicts a first point in time. The tactile pixels 802a-802h may be referred to as an array of tactile pixels. In this example, the arrow has a circular configuration with one "ring" of tactile pixels. The array has a circular configuration with multiple "rings" of tactile pixels, in some embodiments. The rings are not required to have the same number of tactile pixels as each other. Referring again to FIG. 8A, tactile pixel 802a may be referred to as a first end of the array, and tactile pixel 802h may be referred to as a second end of the array.

Tactile pixels 802a-802h are respectively presenting same signal elements S0-S7 as were depicted in the example of FIG. 7A. For example, tactile pixel 802a is presenting signal element S0, tactile pixel 802b is presenting signal element S1, etc. Each signal element is represented by an arrow. The length of the arrow may represent the magnitude of the signal element. In FIGS. 8A-8C, only two different lengths are depicted for the arrows to indicate that each tactile pixel may be in one of two states, in this example. However, the tactile pixels are not required to have binary states. The pattern of signal elements may be referred to as a stimulation pattern. The stimulation pattern has a first end given by S0 and a second end given by S7, at this point in time. As will be discussed below, the stimulation pattern changes over time.

FIG. 8B depicts a second point in time that follows the first point in time. FIG. 8B depicts the immediate next state of the haptic stimulation interface 250 after the state depicted in FIG. 8A, in one embodiment. The haptic stimulation interface 250 now displays signal elements S1-S8. Thus, the stimulation pattern now comprises signal elements S1-S8. Note that signal element S0 (at the first end of the stimulation pattern) has been eliminated and a new portion to the stimulation pattern (S8) has been added to the second end of the stimulation pattern. The stimulation pattern is shown as propagating in the direction from tactile pixel 802h to tactile pixel 802a (as indicated by the arrow below "Stimulation Pattern Propagation"). In other words, the stimulation pattern is propagating in the clockwise direction in this example.

FIG. 8C depicts a third point in time that follows the second point in time. FIG. 8C depicts the immediate next state of the haptic stimulation interface 250 after the state depicted in FIG. 8B, in one embodiment. The haptic stimulation interface 250 now displays signal elements S2-S9. Thus, the stimulation pattern now comprises signal elements S2-S9. Note that signal element S1 (at the first end of the stimulation pattern) has been eliminated and a new portion to the stimulation pattern (S9) has been added to the second end of the stimulation pattern. Again, the stimulation pattern is shown as propagating in the clockwise direction from tactile pixel 802h to tactile pixel 802a (as indicated by the arrow below "Stimulation Pattern Propagation").

Figure 9:
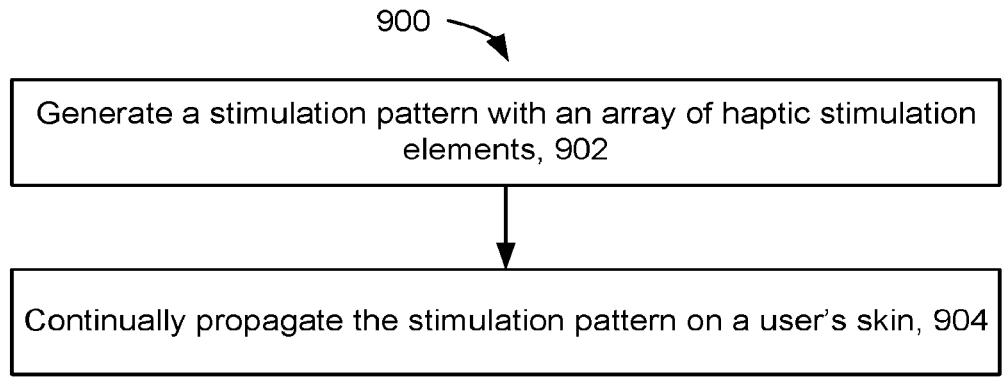
FIG. 9 is a flowchart of an embodiment of a process of providing a haptic stimulation interface.

FIG. 9 is a flowchart of an embodiment of a process 900 of providing a haptic stimulation interface. The process 900 will be described with reference to FIGS. 7A-C and 8A-8C, but is not limited thereto.

Step 902 comprises generating a stimulation pattern with an array comprising haptic stimulation elements. The stimulation pattern may be in contact with a user's skin, such that the stimulation pattern is presented on the user's skin. The stimulation pattern, as presented, comprises a first end and a second end. For example, a stimulation pattern is generated as described with respect to FIG. 7A or 8A. In FIG. 7A, the first end of the stimulation pattern is signal element S0, which is being presented in tactile pixel 702a. In FIG. 8A, the first end of the stimulation pattern is signal element S0, which is being presented in tactile pixel 802a.

Step 904 comprises continually propagating the stimulation pattern on a user's skin. Step 904 may include repeatedly eliminating a portion of the stimulation pattern at the first end of the stimulation pattern and replacing the eliminated portion with a new portion to the stimulation pattern at the second end of the stimulation pattern. In FIG. 7B, signal element S0 (at the first end of the stimulation pattern) has been eliminated and a new portion to the stimulation pattern (S8) has been added to the second end of the stimulation pattern. In FIG. 7C, signal element S1 (at the first end of the stimulation pattern) has been eliminated and a new portion to the stimulation pattern (S9) has been added to the second end of the stimulation pattern. Thus, the stimulation pattern is shown as propagating in the direction from tactile pixel 702*h* to tactile pixel 702*a* (as indicated by the arrow below "Stimulation Pattern Propagation"). There will be some gap in time between the state in FIG. 7A to the state in FIG. 7B. Likewise, there will be some gap in time between the state in FIG. 7B to the state in FIG. 7C. These different states occur at regular intervals, in some embodiments. Thus, the stimulation pattern continually propagates on the user's skin.

In some embodiments, the stimulation pattern is propagated on the user's skin at a constant rate. Propagating the stimulation pattern at a constant rate means that the time gap between successive signal elements touching the same point on the user's skin is constant. For example, with reference to FIGS. 7A-7C, at time t0, signal element S0 is at a specific point on the user's skin; at time t1, signal element S1 is at the specific point on the user's skin; and at time t2, signal element S2 is at the specific point on the user's skin. In some embodiments, the time gap between t0 to t1 is the same as the time gap between t1 and t2, etc. Hence, the stimulation pattern is propagated on the user's skin at a constant rate.

Next the example in FIGS. 8B and 8C will be discussed with respect to step 904. In FIG. 8B, signal element S0 (at the first end of the stimulation pattern) has been eliminated and a new portion to the stimulation pattern (S8) has been added to the second end of the stimulation pattern. In FIG. 8C, signal element S1 (at the first end of the stimulation pattern) has been eliminated and a new portion to the stimulation pattern (S9) has been added to the second end of the stimulation pattern. Thus, the stimulation pattern is shown as propagating in the direction from tactile pixel 802*h* to tactile pixel 802*a* (as indicated by the arrow below "Stimulation Pattern Propagation"). In other words, the stimulation pattern is continually propagating in the clockwise direction in this example.

Figure 10:
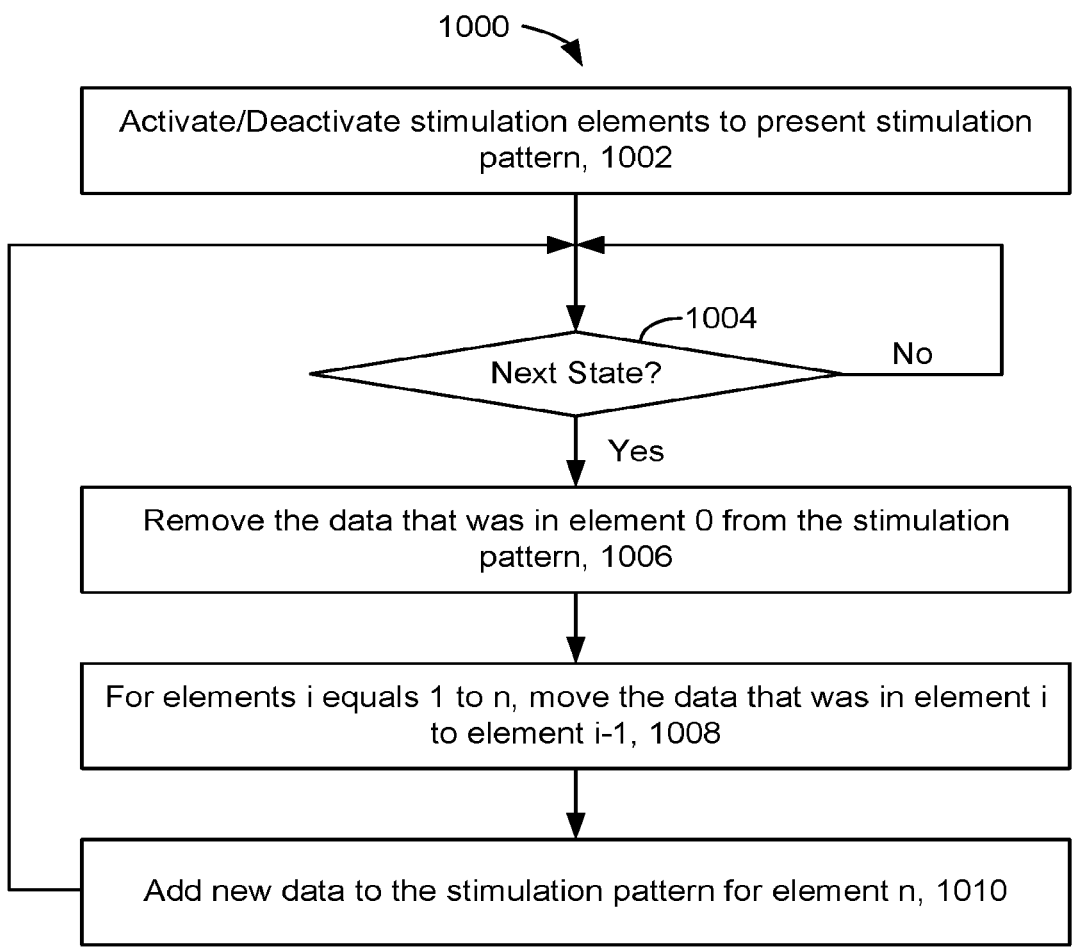
FIG. 10 is a flowchart of one embodiment of a process of continually propagating a stimulation pattern.

FIG. 10 is a flowchart of one embodiment of a process 1000 of continually propagating a stimulation pattern. The process 1000 provides further details of process 900. For the sake of discussion, the haptic stimulation interface has stimulation elements 0 to n (a total of n+1 elements). With respect to the examples of FIGS. 7A-8C, n=7. With respect to the example of FIGS. 7A-7C, element 702*a* is element 0, element 702*b* is element 1, . . . , element 702*n* is element n. With respect to the example of FIGS. 8A-8C, element 802*a* is element 0, element 802*b* is element 1, . . . , element 802*n* is element n.

Step 1002 includes activating or deactivating stimulation elements (or tactile pixels) to present a stimulation pattern. The stimulation pattern may be in contact with a user's skin, such that the stimulation pattern is presented on the user's skin. Step 1004 is a determination of whether to proceed to the next state for the stimulation pattern. In one embodiment, each state is presented for a pre-determined time before moving on to the next state.

Steps 1006-1010 are described in a certain order as a matter of convenience of explanation. These steps could occur simultaneously or in a different order. Step 1006 includes removing data that was in element 0 from the stimulation pattern. By this it is meant that the signal element that was being presented in element 0 for the previous state of the stimulation pattern is no longer a part of the stimulation pattern. For example, going from the state of FIG. 7A to 7B, signal element S0 is no longer presented in the stimulation pattern.

Step 1008 includes, for elements i=1 to n, moving the data that was in element I to element i+1. For example, going from the state of FIG. 7A to 7B, signal element S1 is moved from element 702*b* to 702*a*, signal element S2 is moved from element 702*c* to 702*b*, etc.

Step 1010 includes adding new data to the stimulation pattern for stimulation element n. For example, going from the state of FIG. 7A to 7B, signal element S8 is added to the stimulation pattern at stimulation element 702*h*. The process 1000 then returns to step 1004, such that the present state of the stimulation pattern is presented for a pre-determined time, in one embodiment. Thus, process 1000 depicts an embodiment in which the stimulation pattern is continually propagated.

Figure 18:
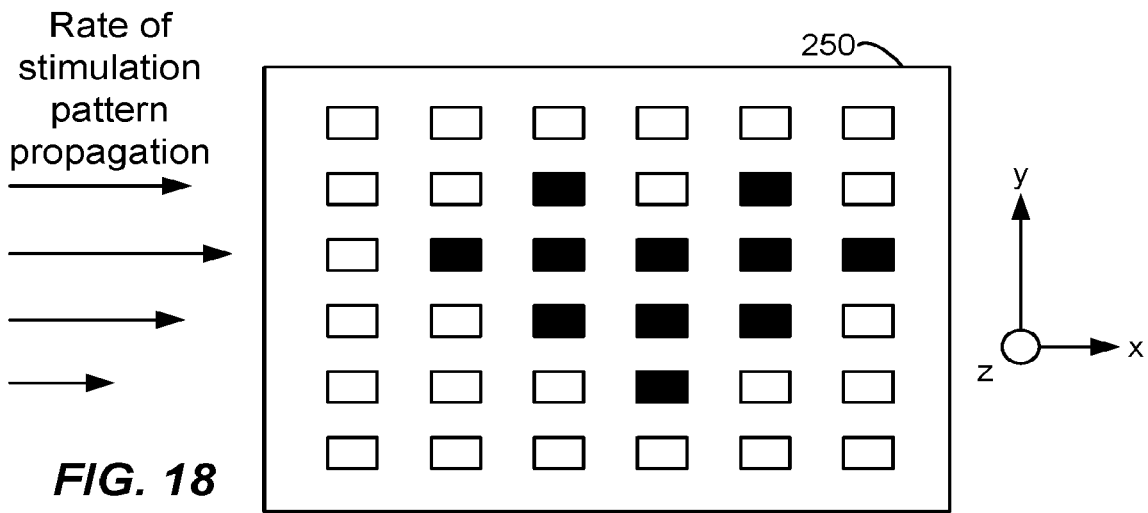
FIG. 18 depicts how a three-dimensional object is represented in one embodiment.
Figure 19:
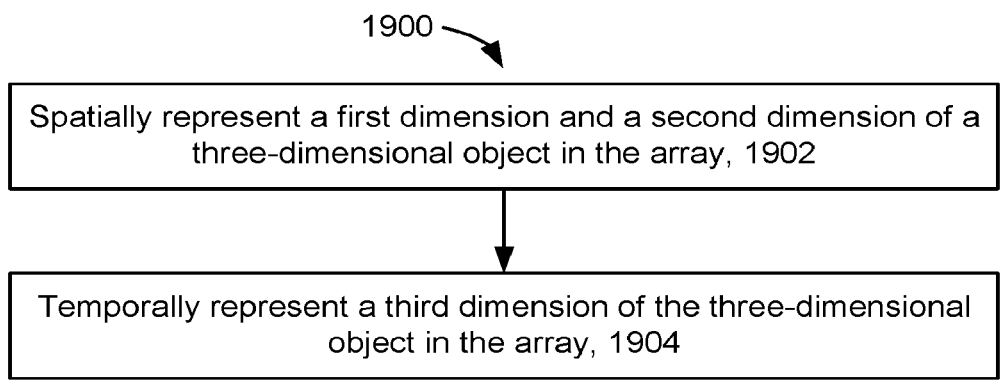
FIG. 19 is a flowchart of one embodiment of a process representing a three-dimensional object in a haptic stimulation interface.
Figure 20:
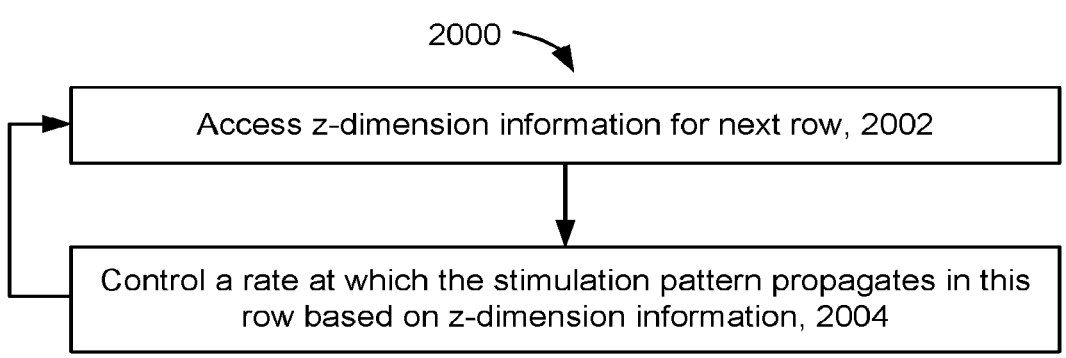
FIG. 20 is a flowchart of one embodiment of a process of temporally representing a third dimension of the object in the array.

FIGS. 9 and 10 were discussed with reference to examples in which the array comprising haptic stimulation elements has a single row. The array comprising haptic stimulation elements has rows and columns of haptic stimulation elements, in some embodiments. In some embodiments, process 900 and/or 1000 the stimulation pattern is propagated at the same rate for each row. In other embodiments, the stimulation pattern is propagated at different rates for different rows. FIGS. 18-20, to be discussed below, describe embodiments in which the stimulation pattern may be propagated at different rates for different rows in order to convey three-dimensional information.

Figure 11A:
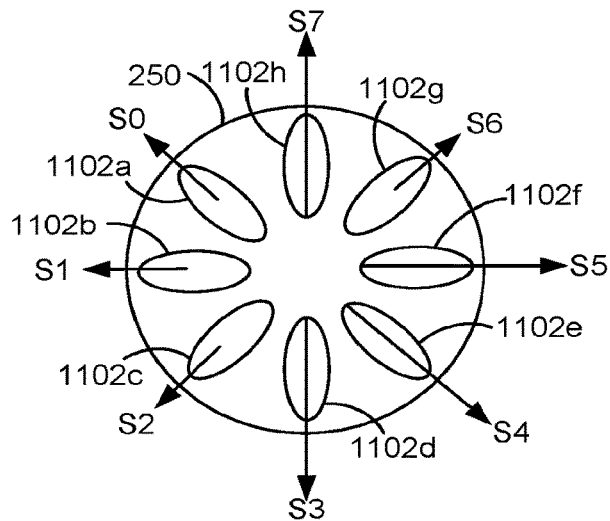
FIGS. 11A-11C depict a haptic stimulation interface at three points in time in order to illustrate an embodiment of propagating a stimulation pattern.
Figure 11B:
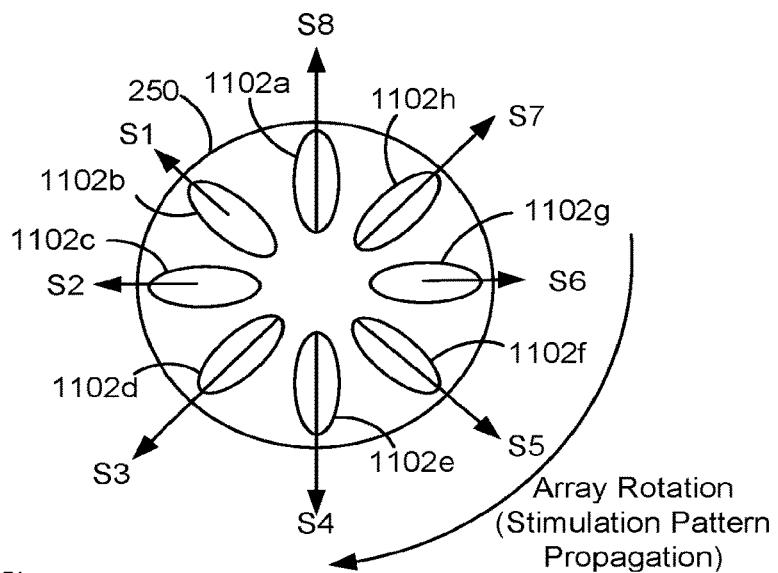
Figure 11C:
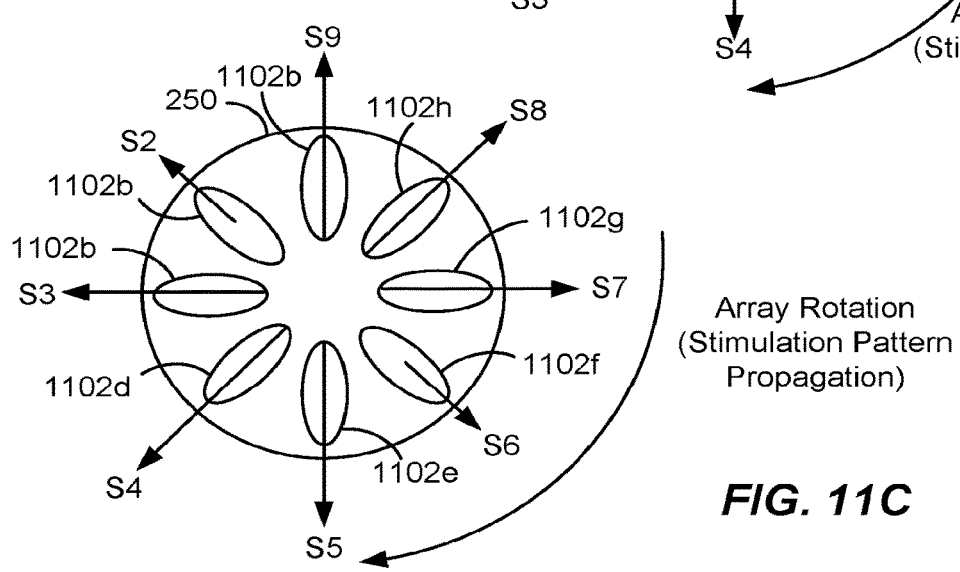

FIGS. 11A-11C depict a haptic stimulation interface 250 at three points in time in order to illustrate an embodiment of propagating a stimulation pattern. The stimulation pattern is propagated on a user's skin, in some embodiment. The user's skin is not expressly depicted in FIGS. 11A-11C. The example stimulation pattern and its propagation is similar to the example of FIGS. 8A-8C. However, haptic stimulation interface 250 rotates in an embodiment depicted in FIGS. 11A-11C. FIGS. 11A-11C depict three different states of the stimulation pattern. The three states occur sequentially at regular intervals, in some embodiments.

FIG. 11A depicts an embodiment of a haptic stimulation interface 250 having eight haptic stimulation elements (or tactile pixels) 1102*a*-1102*h*. The haptic stimulation interface 250 has a similar shape and number of stimulation elements as the embodiment of FIG. 8A. However, different reference numerals are used for the tactile pixels 1102*a*-1102*h* in FIG. 11A. FIG. 11A depicts a first point in time. Tactile pixel 1102*a* may be referred to as a first end of the array, and tactile pixel 1102*h* may be referred to as a second end of the array.

Tactile pixels 1102*a*-1102*h* are respectively presenting same signal elements S0-S7 as were depicted in the example of FIG. 8A. For example, tactile pixel 1102*a* is presenting signal element S0, tactile pixel 1102*b* is presenting signal element S1, etc. Each signal element is represented by an arrow. The length of the arrow may represent the magnitude of the signal element. In FIGS. 11A-11C, only two different lengths are depicted for the arrows to indicate that each tactile pixel may be in one of two states, in this example. However, the tactile pixels are not required to have binary states. The stimulation pattern has a first end given by S0 and a second end given by S7, at this point in time. As will be discussed below, the stimulation pattern changes over time.

FIG. 11B depicts a second point in time that follows the first point in time. FIG. 11B depicts the immediate next state of the haptic stimulation interface 250 after the state depicted in FIG. 11A, in one embodiment. The haptic stimulation interface 250 now displays signal elements S1-S8. Thus, the stimulation pattern now comprises signal elements S1-S8. Note that signal element S0 (at the first end of the stimulation pattern) has been eliminated and a new portion to the stimulation pattern (S8) has been added to the second end of the stimulation pattern. The array is depicted as rotating in the clockwise direction. For example, tactile pixel 1102a is at the 12 o-clock position in FIG. 11B, whereas tactile pixel 1102h was at the 12 o-clock position in FIG. 11A.

FIG. 11C depicts a third point in time that follows the second point in time. FIG. 11C depicts the immediate next state of the haptic stimulation interface 250 after the state depicted in FIG. 11B, in one embodiment. The haptic stimulation interface 250 now displays signal elements S2-S9. Thus, the stimulation pattern now comprises signal elements S2-S9. Note that signal element S1 (at the first end of the stimulation pattern) has been eliminated and a new portion to the stimulation pattern (S9) has been added to the second end of the stimulation pattern. Again, the array is shown as rotating in the clockwise direction. Therefore, the stimulation pattern also rotates in the clockwise pattern. Moreover, the stimulation pattern is rotated across the user's skin in this example.

Figure 12:
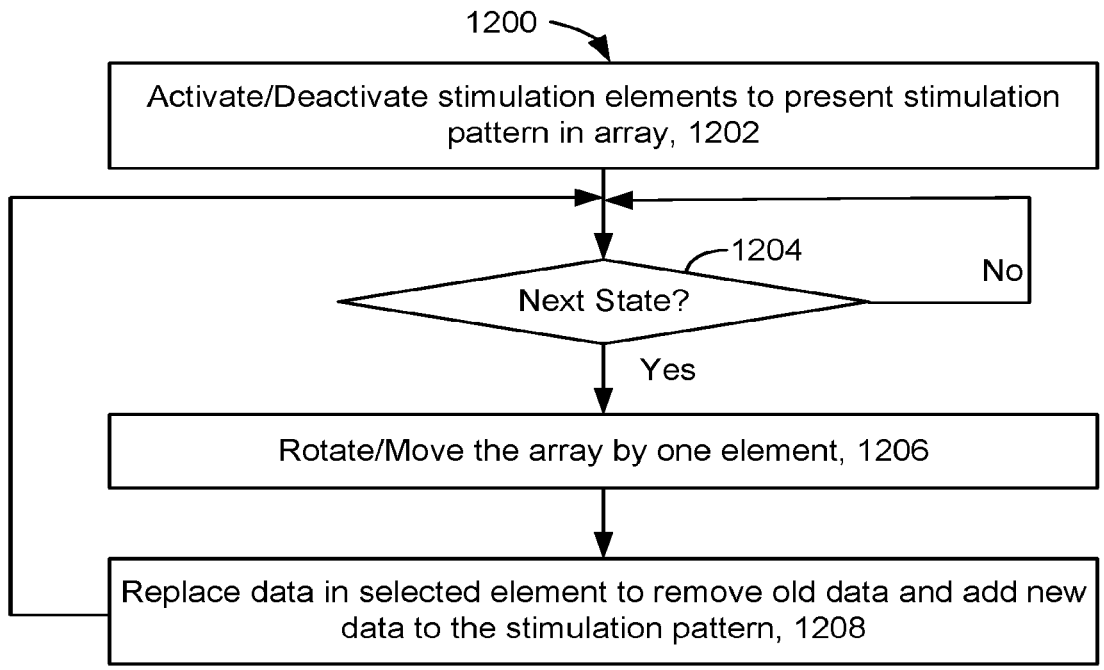
FIG. 12 is a flowchart of one embodiment of a process of continually propagating a stimulation pattern.

FIG. 12 is a flowchart of one embodiment of a process 1200 of continually propagating a stimulation pattern. The process 1200 provides further details of process 900. For the sake of discussion, the haptic stimulation interface has stimulation elements 0 to n (a total of n+1 elements). With respect to the examples of FIGS. 11A-11C, n=7. With respect to the example of FIGS. 11A-11C, element 1102a is element 0, element 1102b is element 1, . . . , element 1102n is element n.

Step 1202 includes activating or deactivating stimulation elements (or tactile pixels) to present a stimulation pattern. The stimulation pattern may be in contact with a user's skin, such that the stimulation pattern is presented on the user's skin. FIG. 11A depicts one example of step 1202. Step 1204 is a determination of whether to proceed to the next state for the stimulation pattern. In one embodiment, each state is presented for a pre-determined time before moving on to the next state.

Steps 1206-1208 are described in a certain order as a matter of convenience of explanation. These steps could occur simultaneously or in a different order. Step 1208 includes rotating or moving the haptic stimulation interface 250 by one stimulation element. For example, going from the state of FIG. 11A to 11B, the haptic stimulation interface 250 is rotated clockwise by one stimulation element.

Step 1208 includes replacing data in a selected element to remove old data and add new data to the stimulation pattern. For example, a comparison of FIGS. 11A and 11B shows signal element S0 being replaced by signal element S8 in tactile pixel 1102a. As another example, a comparison of FIGS. 11B and 11C shows signal element S1 being replaced by signal element S9 in tactile pixel 1102b.

The process 1200 then returns to step 1204, such that the present state of the stimulation pattern is presented for a pre-determined time, in one embodiment. Thus, process 1200 depicts an embodiment in which the stimulation pattern is continually propagated.

Figure 13:
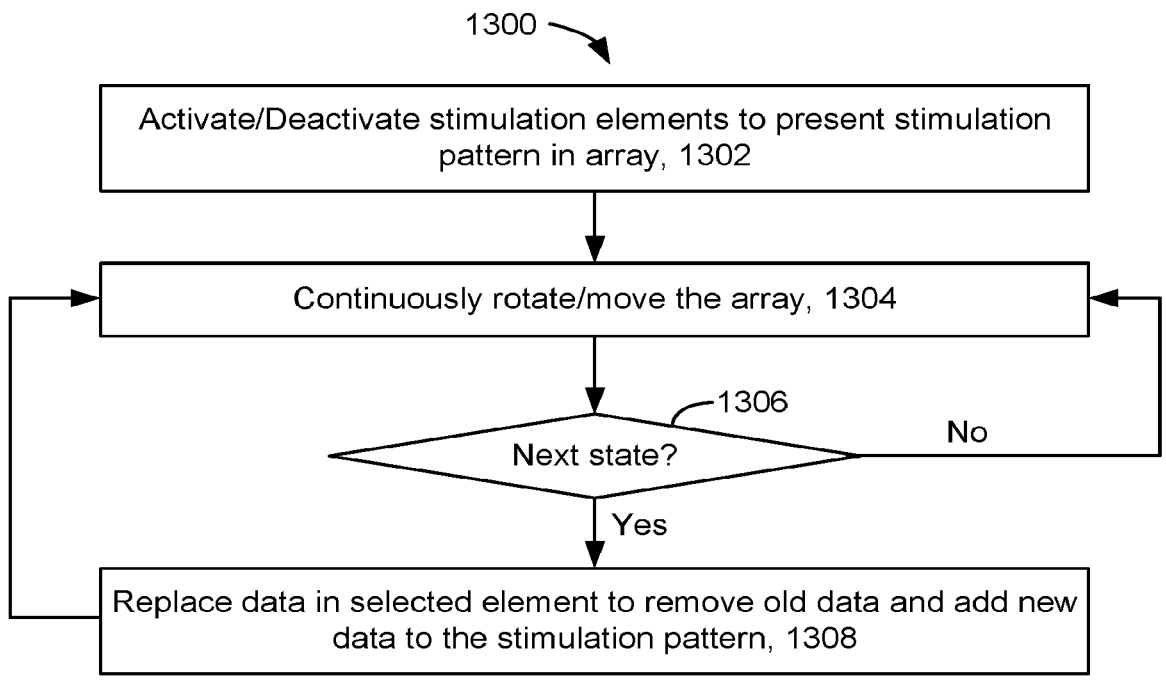
FIG. 13 depicts another embodiment of a process of continually propagating a stimulation pattern.

FIG. 13 depicts another embodiment of a process 1300 of continually propagating a stimulation pattern. The process 1300 provides further details of process 900. The process 1300 is a variation of process 1200 in which the array rotation is continuous. The term "continuous" or "continuously," as used herein means "without interruption." This is in contrast with an embodiment of process 1200 in which the array is "stepped" from one state to the next.

Step 1302 includes activating or deactivating stimulation elements (or tactile pixels) to present a stimulation pattern. The stimulation pattern may be in contact with a user's skin, such that the stimulation pattern is presented on the user's skin. FIG. 11A depicts one example of step 1302. Step 1304 includes continuously rotating the array. The array is continuously rotated at a constant angular velocity, in one embodiment.

Step 1306 is a determination of whether it is time to change the state of the stimulation pattern. Step 1306 may be similar to step 1204 in that a new state may be presented after a pre-determined period of time.

Step 1308 includes replacing data in a selected element to remove old data and add new data to the stimulation pattern. For example, a comparison of FIGS. 11A and 11B shows signal element S0 being replaced by signal element S8 in tactile pixel 1102a. As another example, a comparison of FIGS. 11B and 11C shows signal element S1 being replaced by signal element S9 in tactile pixel 1102b.

The process 1300 is then depicted as returning to step 1304. Note that step 1304 may actually continue to be performed throughout the process. In other words, it is not required that rotation of the array stop during process 1300. Thus, process 1300 depicts an embodiment in which the stimulation pattern is continually propagated.

Figure 14A:
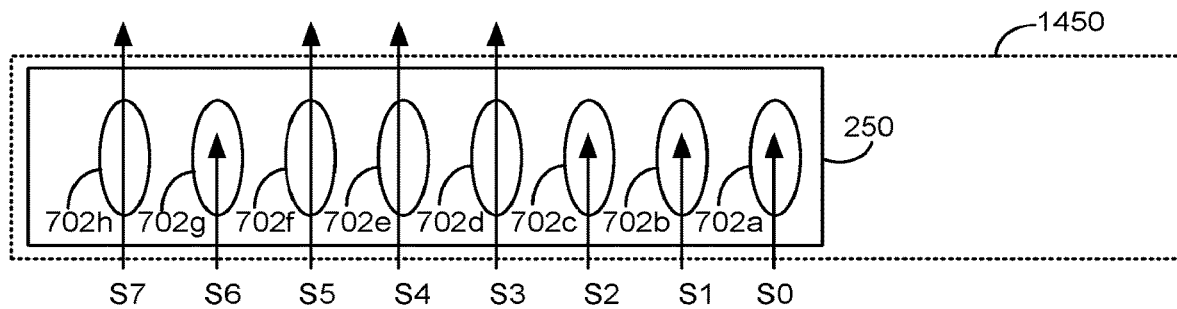
FIGS. 14A-14F depict an embodiment of a haptic stimulation interface at six points in time in order to illustrate an embodiment of propagating a stimulation pattern.

FIGS. 14A-14F depict an embodiment of a haptic stimulation interface 250 at six points in time in order to illustrate an embodiment of propagating a stimulation pattern. The haptic stimulation interface 250 is physically moved across the user's skin in this embodiment. The haptic stimulation interface 250 is similar to the one of FIG. 7A, hence the same reference numerals are used for the tactile pixels 702a-702h. FIG. 14A shows the same stimulation pattern as shown in FIG. 7A. The dotted box labeled 1450 represents the user's skin, which is in contact with the tactile pixels 702a-702h.

Figure 14B:
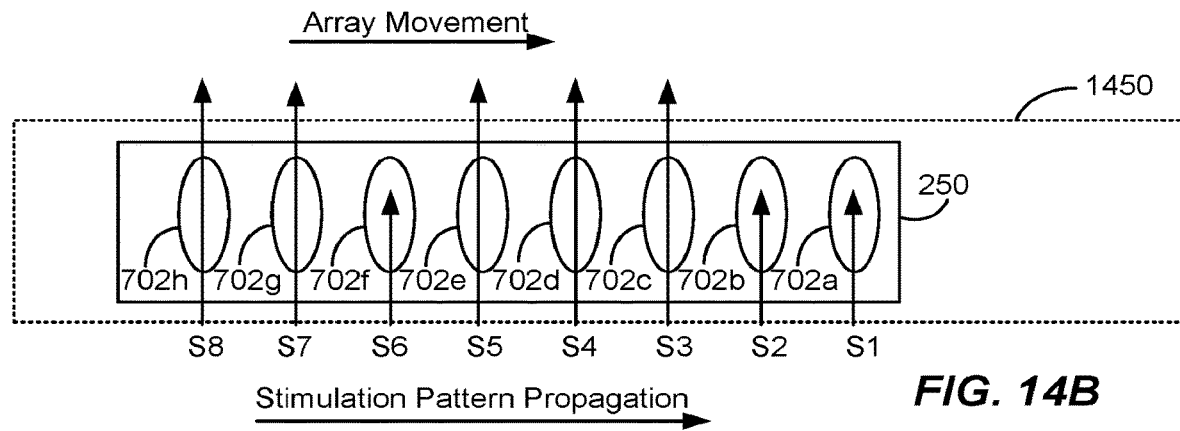

FIG. 14B depicts a second point in time that follows the first point in time depicted in FIG. 14A. FIG. 14B depicts the immediate next state of the haptic stimulation interface 250 after the state depicted in FIG. 14A, in one embodiment. The haptic stimulation interface 250 has moved as indicated by the arrow labeled "Array Movement." Therefore, the haptic stimulation interface 250 is being moved across the user's skin 1450. The haptic stimulation interface 250 now displays signal elements S1-S8. Thus, the stimulation pattern now comprises signal elements S1-S8. Note that signal element S0 (at the first end of the stimulation pattern) has been eliminated and a new portion to the stimulation pattern (S8) has been added to the second end of the stimulation pattern. The stimulation pattern is shown as propagating in the direction from tactile pixel 702h to tactile pixel 702a (as indicated by the arrow below "Stimulation Pattern Propagation").

Figure 14C:
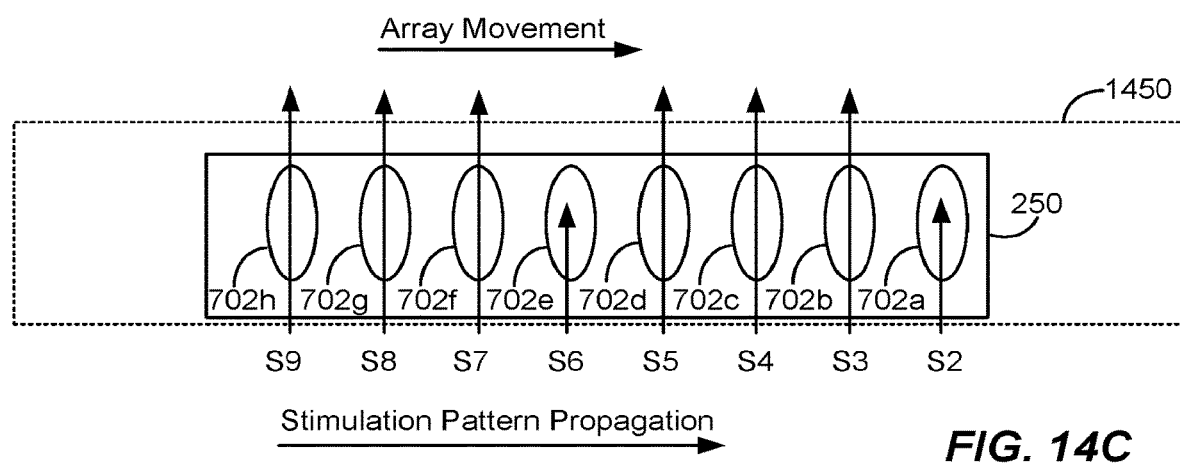

FIG. 14C depicts a third point in time that follows the second point in time. FIG. 14C depicts the immediate next state of the haptic stimulation interface 250 after the state depicted in FIG. 14B, in one embodiment. The haptic stimulation interface 250 has moved further as indicated by the arrow labeled "Array Movement." Therefore, the haptic stimulation interface 250 is being moved across the user's skin 1450. The haptic stimulation interface 250 now displays signal elements S2-S9. Thus, the stimulation pattern now comprises signal elements S2-S9. Note that signal element S1 (at the first end of the stimulation pattern) has been eliminated and a new portion to the stimulation pattern (S9) has been added to the second end of the stimulation pattern. Again, the stimulation pattern is shown as propagating in the direction from tactile pixel 702*h* to tactile pixel 702*a* (as indicated by the arrow below "Stimulation Pattern Propagation").

Figure 14D:
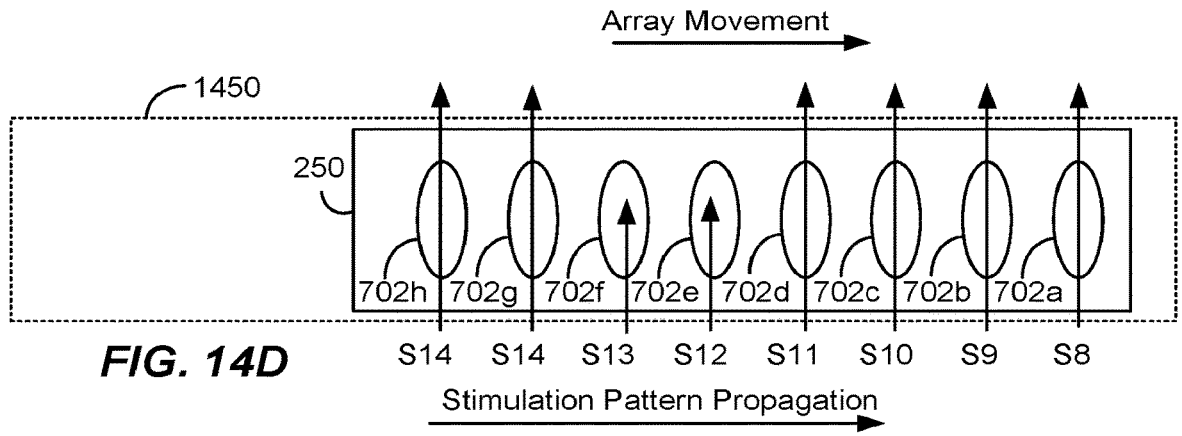

FIG. 14D depicts a point in time that follows the third point in time. However, FIG. 14D does not depict the immediate next state of the haptic stimulation interface 250 after the state depicted in FIG. 14C. Rather, several intermediate states are not depicted. The haptic stimulation interface 250 has moved still further across the user's skin 1450 as indicated by the arrow labeled "Array Movement." The haptic stimulation interface 250 now displays signal elements S8-S14. Thus, the stimulation pattern now comprises signal elements S8-S14. Again, the stimulation pattern is shown as propagating in the direction from tactile pixel 702*h* to tactile pixel 702*a* (as indicated by the arrow below "Stimulation Pattern Propagation").

Figure 14E:
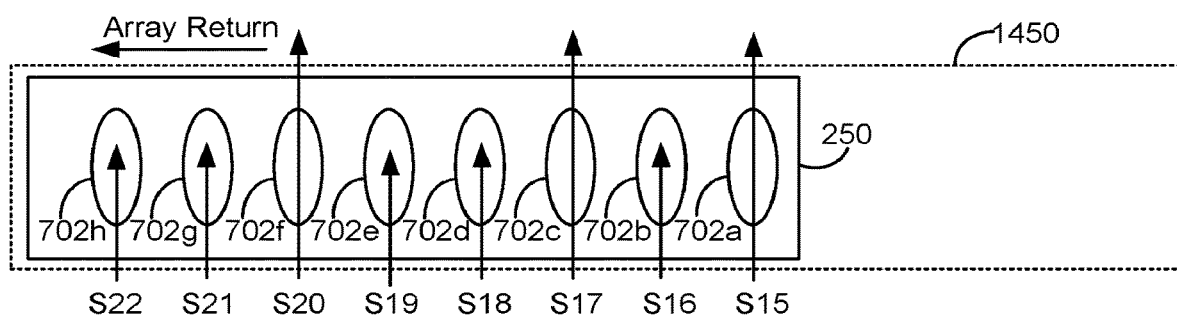

FIG. 14E depicts a point in time that follows the point in time depicted in FIG. 14D. FIG. 14E depicts the immediate next state of the haptic stimulation interface 250 after the state depicted in FIG. 14D, in one embodiment. The haptic stimulation interface 250 has moved back to its position of FIG. 14A. However, now the haptic stimulation interface 250 comprises signal elements S15-S22. In this state transition, all of the signal elements depicted in FIG. 14D have been replaced.

Figure 14F:
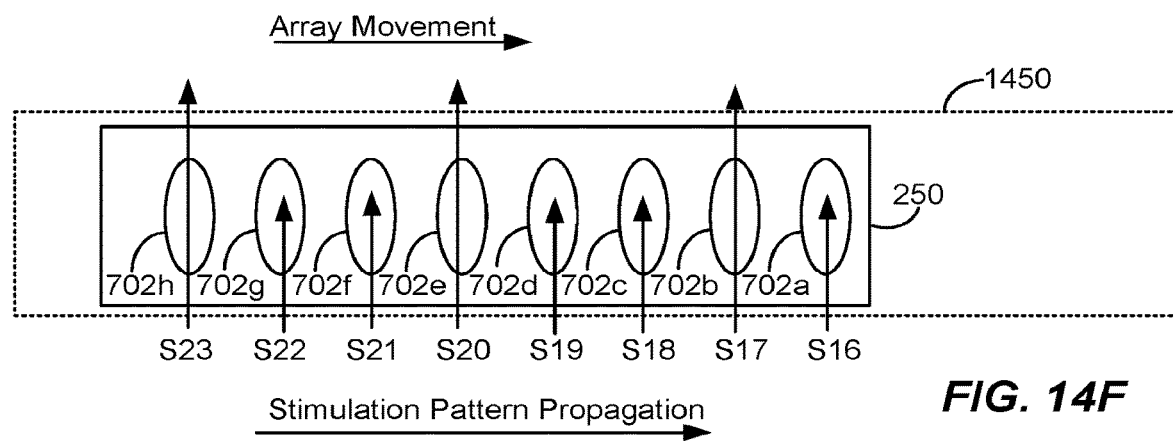

FIG. 14F depicts a point in time that follows the point in time depicted in FIG. 14E. FIG. 14F depicts the immediate next state of the haptic stimulation interface 250 after the state depicted in FIG. 14E, in one embodiment. The haptic stimulation interface 250 has moved as indicated by the arrow labeled "Array Movement." Therefore, the haptic stimulation interface 250 is being moved across the user's skin 1450. The haptic stimulation interface 250 now displays signal elements S16-S23.

Figure 15:
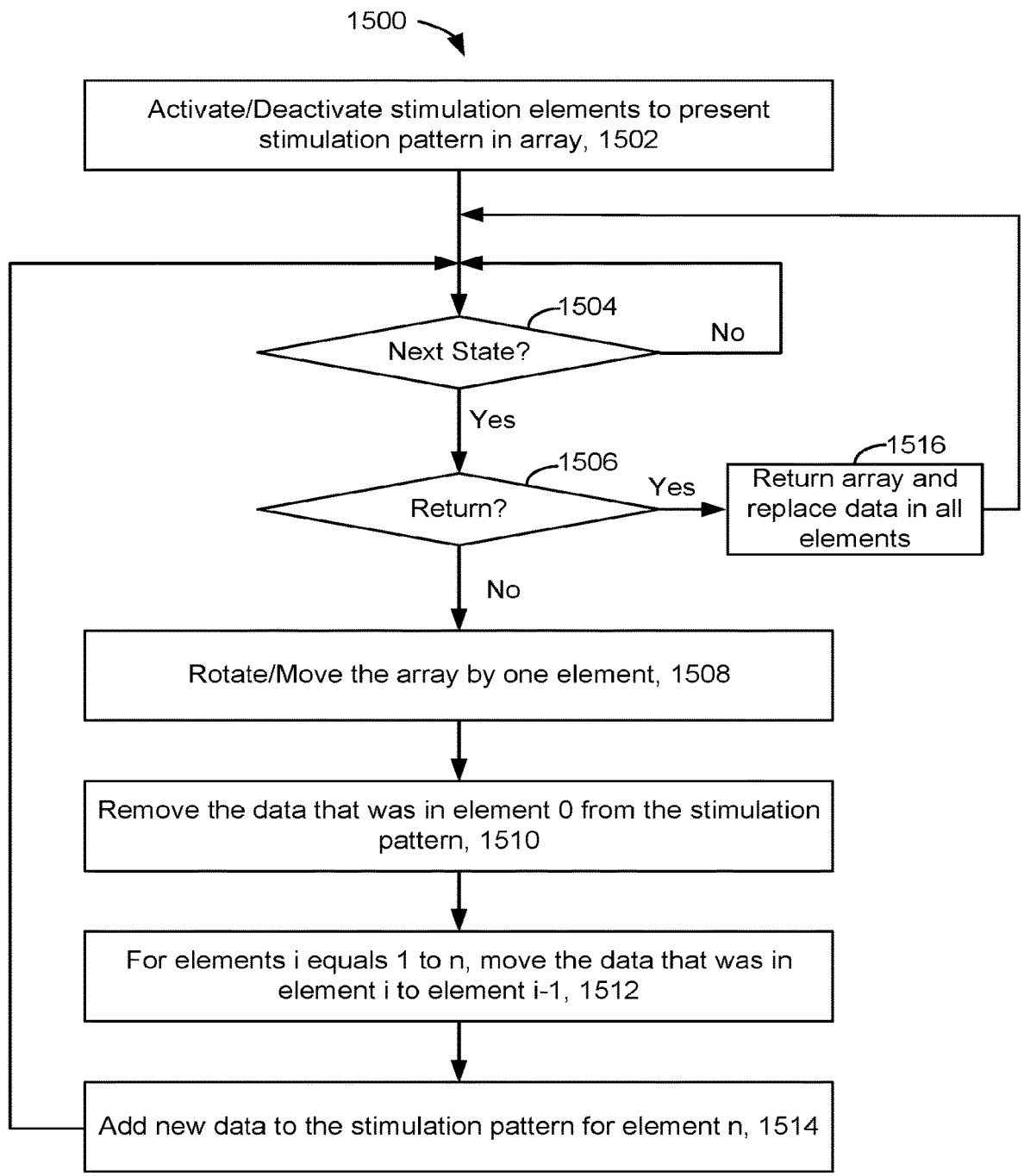
FIG. 15 is a flowchart of one embodiment of a process of continually propagating a stimulation pattern.

FIG. 15 is a flowchart of one embodiment of a process 1500 of continually propagating a stimulation pattern. The process 1500 provides further details of process 900. For the sake of discussion, the haptic stimulation interface has stimulation elements 0 to n (a total of n+1 elements). With respect to the example of FIGS. 14A-14F, n=7. With respect to the example of FIGS. 14A-14C, element 702*a* is element 0, element 702*b* is element 1, . . . , element 702*n* is element n.

Step 1502 includes activating or deactivating stimulation elements (or tactile pixels) to present a stimulation pattern. The stimulation pattern may be in contact with a user's skin, such that the stimulation pattern is presented on the user's skin. Step 1504 is a determination of whether to proceed to the next state for the stimulation pattern. In one embodiment, each state is presented for a pre-determined time before moving on to the next state. Step 1506 is a determination of whether to return the array to the starting position. An example of the return is depicted in the transition from the state of FIG. 14D to the state of FIG. 14E. Assuming the array is not to be returned to the starting position, steps 1508-1514 are performed.

Steps 1508-1514 are described in a certain order as a matter of convenience of explanation. These steps could occur simultaneously or in a different order. Step 1508 includes rotating or moving the array by one stimulation element. For example, with reference to FIGS. 14A and 14B, the haptic stimulation interface 250 may be moved one stimulation element to the right from FIG. 14A to 14B. As another example, the haptic stimulation interface 250 may be rotated, as depicted in FIGS. 11A-11C.

Step 1510 includes removing data that was in element 0 from the stimulation pattern. By this it is meant that the signal element that was being presented in element 0 for the previous state of the stimulation pattern is no longer a part of the stimulation pattern. For example, going from the state of FIG. 14A to 14B, signal element S0 is no longer presented in the stimulation pattern.

Step 1512 includes, for elements i=1 to n, moving the data that was in element i to element i+1. For example, going from the state of FIG. 14A to 14B, signal element S1 is moved from element 702*b* to 702*a*, signal element S2 is moved from element 702*c* to 702*b*, etc.

Step 1514 includes adding new data to the stimulation pattern for stimulation element n. For example, going from the state of FIG. 14A to 14B, signal element S8 is added to the stimulation pattern at stimulation element 702*h*.

The process 1500 then returns to step 1504, such that the present state of the stimulation pattern is presented for a pre-determined time, in one embodiment. As noted above, step 1506 is a determination of whether to return the array to the starting position. Step 1516 is performed to return the array after the array has been moved to its furthermost extent, in one embodiment. Thus, process 1500 depicts an embodiment in which the stimulation pattern is continually propagated on user's skin.

Figure 16A:
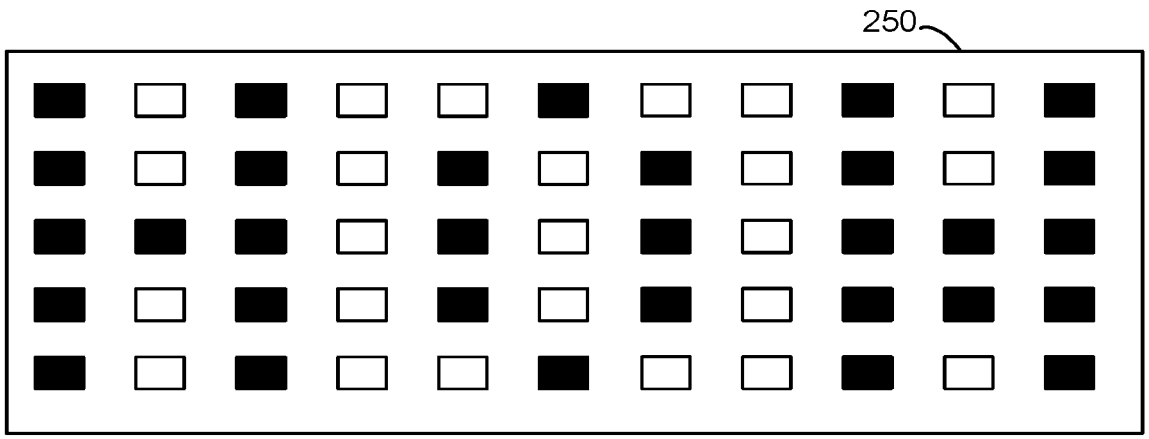
FIGS. 16A-16E depict one embodiment of displaying a message in a haptic stimulation interface.
Figure 16B:
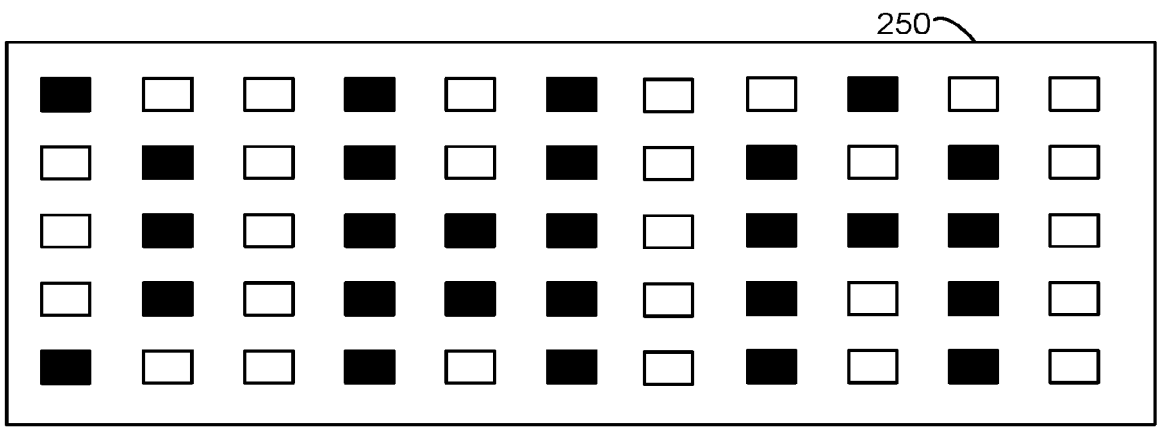

FIGS. 16A-16E depict one embodiment of displaying a message in a haptic stimulation interface. The message "how are you" is presented over time. FIGS. 16A-16E show five different states for the stimulation pattern that contains the message. Other intermediate states are not depicted. In FIG. 16A, the word "how" is being presented in the haptic stimulation interface 250. In FIG. 16B, the letter "h" and a portion of the letter "o" have been removed from the stimulation pattern. A portion of the letter "o" and the letter "h" remain in the stimulation pattern, but are in a different location in the stimulation interface 250. Also, the letter "a" has been added to the stimulation pattern. There may be numerous states between the states depicted in FIGS. 16A and 16B in which the stimulation pattern progressively changes. For example, the pattern may change one column at a time.

Figure 16C:
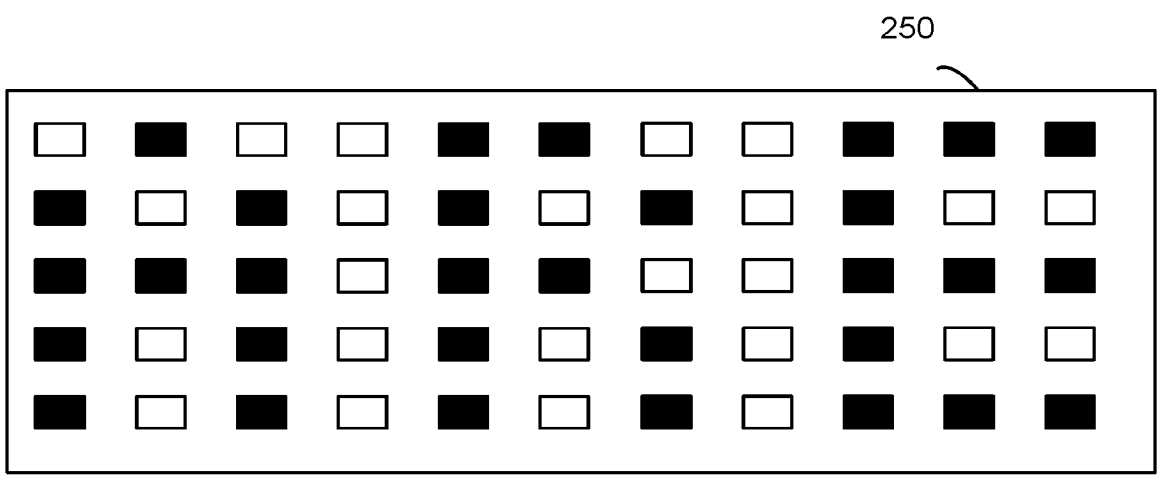

FIG. 16C depicts a later state in which the word "are" is being presented in the stimulation interface 250. Note that the stimulation pattern does not go from the state of FIG. 16A directly to the state of FIG. 16C, in this embodiment. Rather, there are states in which only some of the letters from the word "are" are presented. In some states, a portion of a letter from the word "are" may be presented. This technique may allow the user to interpret the content of the stimulation pattern faster. For example, the user may be able to anticipate a word that may follow the word "how". Thus, even if the complete word "are" is not presented in the haptic stimulation interface 250, the user may anticipate what letters or words are coming next.

Figure 16D:
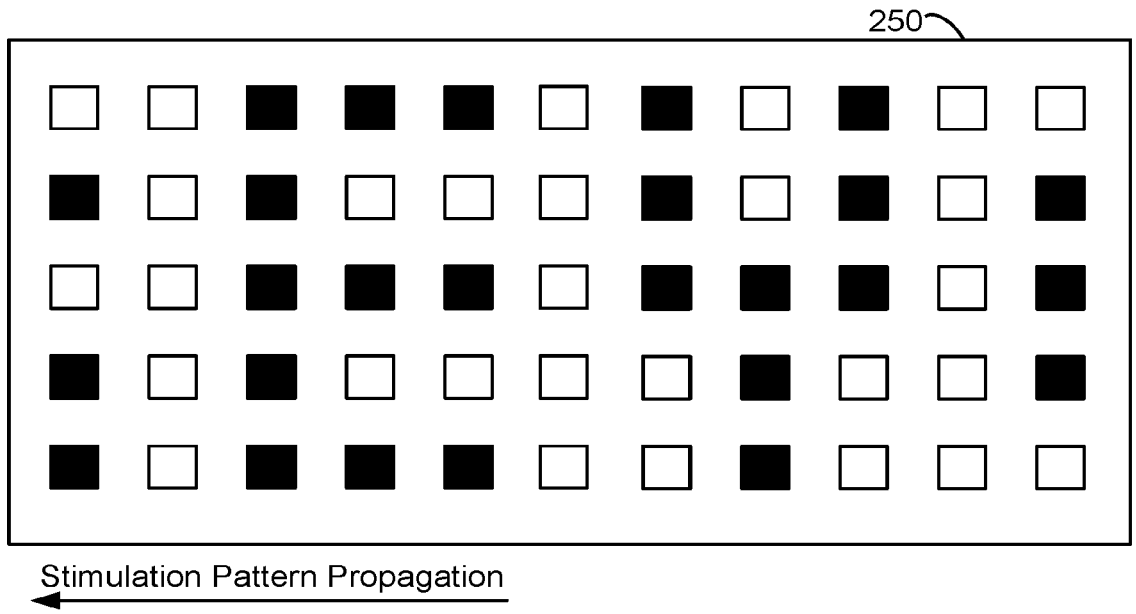
Figure 16E:
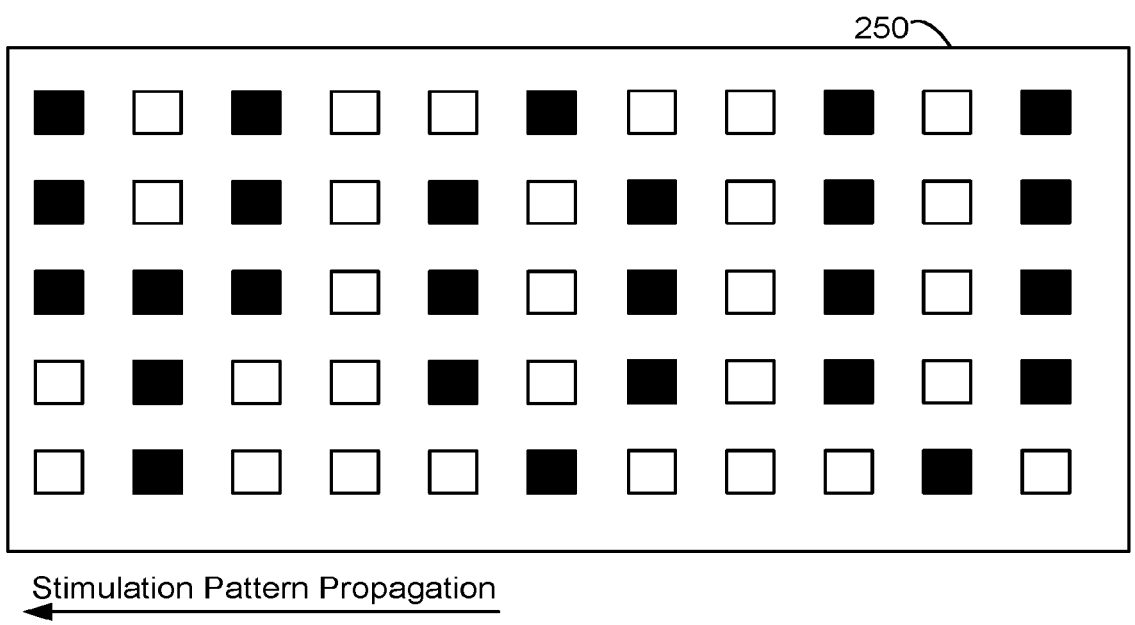

FIGS. 16D and 16E depict two later states. FIG. 16E depicts the word "you" in the haptic stimulation interface 250. FIG. 16D depicts a state in which part of the word "are" and part of the word "you" are being presented. In this example, the user may be able to anticipate that the word "you" is going to follow "are". Thus, even with partial information of the word "you" entering the pattern, the user can begin to decipher the content.

Note that FIGS. 16B and 16D contain examples of presenting two partial units of information at the same time in the stimulation pattern. For example, in FIG. 16B, a part of the word "how" (one unit of information) and a part of the word "are" (another unit of information) are presented at the same time in the stimulation pattern. As another example, in FIG. 16D, a part of the word "are" (one unit of information) and a part of the word "you" (another unit of information) are presented at the same time in the stimulation pattern. Also, in FIG. 16D, a part of the letter "R" (one unit of information) and a part of the letter "O" (another unit of information) are presented at the same time in the stimulation pattern. A "partial unit of information" is defined herein as information that by itself does not convey its intended meaning due to being incomplete. Thus, by themselves these partial units of information might not be understood by the user. However, due to the continual propagation of the stimulation pattern, the user may be able to discern meaning even in partial units of information. This applies to both partial units of information that are leaving the stimulation pattern, as well as partial units of information that are entering the stimulation pattern.

Figure 17:
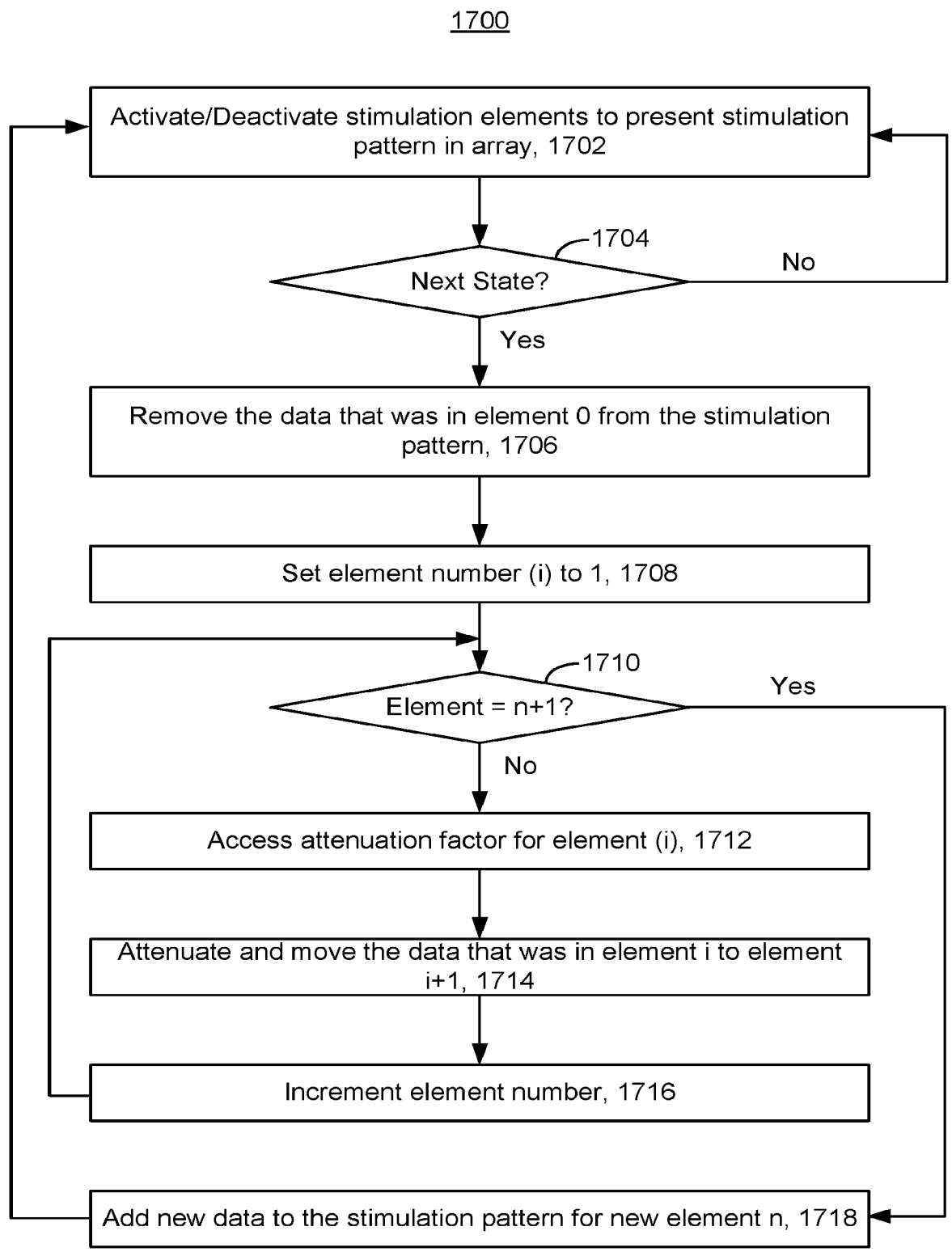
FIG. 17 is a flowchart of one embodiment of a process in which data in the stimulation pattern is attenuated.

In some embodiments, a long short-term memory model (LSTM model) is used to control how the stimulation pattern is modified over time. As the stimulation pattern is propagated, the signal elements can be modified (e.g., attenuated, augmented, dropped, added, etc.) based on the LSTM model. An LSTM module may have an input gate, an output gate, and a forget gate. These three gates may compute their respective outputs based on both a present time step (e.g., t) and a previous time step (e.g., t−1). In some embodiments, various weights can be applied to the gates to impact how that gate contributes to the final output of the LSTM module. In some embodiments, portions of the stimulation pattern are attenuated over time. FIG. 17 is a flowchart of one embodiment of a process 1700 in which data in the stimulation pattern is attenuated. In one embodiment, process 1700 is based on a LSTM model. For the sake of discussion, the haptic stimulation interface has stimulation elements 0 to n (a total of n+1 elements). With respect to the examples of FIGS. 7A-8C, n=7. With respect to the example of FIGS. 7A-7C, element 702a is element 0, element 702b is element 1, . . . , element 702n is element n. With respect to the example of FIGS. 8A-8C, element 802a is element 0, element 802b is element 1, . . . , element 802n is element n.

Step 1702 includes activating or deactivating stimulation elements (or tactile pixels) to present a stimulation pattern. The stimulation pattern may be in contact with a user's skin, such that the stimulation pattern is presented on the user's skin. Step 1704 is a determination of whether to proceed to the next state for the stimulation pattern. In one embodiment, each state is presented for a pre-determined time before moving on to the next state.

Step 1706 includes removing data that was in element 0 from the stimulation pattern. By this it is meant that the signal element that was being presented in element 0 for the previous state of the stimulation pattern is no longer a part of the stimulation pattern. For example, going from the state of FIG. 7A to 7B, signal element S0 is no longer presented in the stimulation pattern.

Step 1708 includes setting an element number to 1. Step 1710 is a test of whether the old element number equals n+1. This test is to determine whether all elements in the array have been processed. The process 1700 continues at step 1712 if step 1710 is not true. In step 1712, an attenuation factor is accessed for the current element being processed. Each element may have its own attenuation factor. The attenuation factor is between 0 and 1 (inclusive), in one embodiment. An attenuation factor of 0 results in dropping a signal element, in one embodiment. In another embodiment, rather than attenuating, an augmenting factor is used. That is, the factor may be greater than 1 for some elements, in one embodiment.

Step 1714 includes, attenuating and moving the data that was in element i to element i+1. For example, going from the state of FIG. 7A to 7B, signal element S1 is attenuated and moved from element 702b to 702a. Step 1716 includes incrementing the element number. The process returns to step 1710. This time through the loop, signal element S2 may be attenuated and moved from element 702c to 702b, for example. The attenuation factor applied to signal S2 may be greater than, the same, or less than the attenuation factor applied to signal S1.

After all elements have been processed (step 1710=yes), the process continues at step 1718. Step 1718 includes adding new data to the stimulation patter for the new element. For example, going from the state of FIG. 7A to 7B, signal element S8 is added at tactile pixel 702h. Note that over time, a given signal may be attenuated multiple times as the signal is propagated through the array.

In some embodiments, a three-dimensional object is represented in the array comprising haptic stimulation interface 250. FIG. 18 depicts how a three-dimensional object is represented in one embodiment. The haptic stimulation interface 250 comprises a two-dimensional array of tactile pixels, which are used to present two dimensions of the object. In this example, two dimensions (e.g., x, y) of a heart are being presented. The third dimension (e.g., z) is presented by the rate of propagation of the stimulation pattern, in this embodiment. In particular, the rate at which the stimulation pattern is propagated in the x-direction defines depth (or z-dimension) information, in one embodiment. The stimulation pattern may be propagated at a different rate in each row.

FIG. 19 is a flowchart of one embodiment of a process 1900 representing a three-dimensional object in a haptic stimulation interface 250. Step 1902 includes spatially representing a first dimension and a second dimension of a three-dimensional object in the array. With reference to FIG. 18, an x-dimension and a y-dimension of the object are presented by the tactile pixels. The first dimension and a second dimension may be part of a stimulation pattern. The stimulation pattern may be in contact with a user's skin, such that the stimulation pattern is presented on the user's skin.

Step 1904 includes temporally representing a third dimension of the object in the array. With reference to FIG. 18, the rate of propagation in each row of the array may be used to convey depth information. Thus, the rate of propagation of different regions of the rate of propagation may be used to convey depth information.

FIG. 20 is a flowchart of one embodiment of a process 2000 of temporally representing a third dimension of the object in the haptic stimulation interface 250. Process 2000 provides further details for one embodiment of step 1904. Step 2002 includes accessing z-dimension information for a row of the haptic stimulation interface 250. In one embodiment, the z-dimension information is a constant value that may represent an average depth for the row. In one embodiment, the z-dimension information is an array of values that each represent a depth (or z-dimension) for a point on the object.

Step 2004 includes controlling a rate at which the stimulation pattern propagates in this row based on the z-dimension information. In one embodiment, a faster rate of propagation corresponds to the object being closer in the z-direction to a reference point of the user. In one embodiment, the rate of propagation is constant to indicate an average depth for that row. In one embodiment, the rate of propagation changes to indicate changing depth for that row. In this latter embodiment, the rate of propagation can be based on the aforementioned array of values that each represent a depth (or z-dimension) for a point on the object. In this latter embodiment, each depth value in the array can be used once, or the depth values in the array can be cycled over and over as long as the three-dimensional object is presented in the haptic stimulation interface 250. The process then returns to step 2002 to process the next row in the array. Note that process 2000 describes processing each row separately as a matter of convenience of explanation. The processing of each row may be performed in parallel.

The technology described herein can be implemented using hardware, software, or a combination of both hardware and software. The software used is stored on one or more of the processor readable storage devices described above to program one or more of the processors to perform the functions described herein. The processor readable storage devices can include computer readable media such as volatile and non-volatile media, removable and non-removable media. By way of example, and not limitation, computer readable media may comprise computer readable storage media and communication media. Computer readable storage media may be implemented in any method or technology for storage of information such as computer readable instructions, data structures, program modules or other data. Computer readable storage media is an example of a non-transitory computer-readable medium. Examples of computer readable storage media include RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by a computer. A computer readable medium or media does (do) not include propagated, modulated or transitory signals.

Communication media typically embodies computer readable instructions, data structures, program modules or other data in a propagated, modulated or transitory data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as RF and other wireless media. Combinations of any of the above are also included within the scope of computer readable media.

In alternative embodiments, some or all of the software can be replaced by dedicated hardware control circuit components. For example, and without limitation, illustrative types of hardware control circuit components that can be used include Field-programmable Gate Arrays (FPGAs), Application-specific Integrated Circuits (ASICs), Application-specific Standard Products (ASSPs), System-on-a-chip systems (SOCs), Complex Programmable Control Circuit Devices (CPLDs), special purpose computers, etc. In one embodiment, software (stored on a storage device) implementing one or more embodiments is used to program one or more processors. The one or more processors can be in communication with one or more computer readable media/storage devices, peripherals and/or communication interfaces.

It is understood that the present subject matter may be embodied in many different forms and should not be construed as being limited to the embodiments set forth herein. Rather, these embodiments are provided so that this subject matter will be thorough and complete and will fully convey the disclosure to those skilled in the art. Indeed, the subject matter is intended to cover alternatives, modifications and equivalents of these embodiments, which are included within the scope and spirit of the subject matter as defined by the appended claims. Furthermore, in the following detailed description of the present subject matter, numerous specific details are set forth in order to provide a thorough understanding of the present subject matter. However, it will be clear to those of ordinary skill in the art that the present subject matter may be practiced without such specific details.

Aspects of the present disclosure are described herein with reference to flowchart illustrations and/or block diagrams of methods, apparatuses (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

For purposes of this document, each process associated with the disclosed technology may be performed continuously and by one or more computing devices. Each step in a process may be performed by the same or different computing devices as those used in other steps, and each step need not necessarily be performed by a single computing device.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims.

What is claimed is:

1. A haptic interface device, comprising:
an array comprising haptic stimulation elements configured to generate a stimulation pattern; and
a controller configured to continually propagate the stimulation pattern on a user's skin by repeatedly eliminating a portion of a first end of the stimulation pattern and replacing the portion eliminated with a new portion at a second end of the stimulation pattern.

2. The haptic interface device of claim 1, wherein the controller is configured to propagate the stimulation pattern at a constant rate on the user's skin, wherein the array comprises rows and columns of the haptic stimulation elements, and wherein the controller is configured to propagate the stimulation pattern at a same rate for each row.

3. The haptic interface device of claim 1, wherein the controller is configured to propagate the stimulation pattern at a constant rate on the user's skin, wherein the array comprises rows and columns of the haptic stimulation elements, and wherein the controller is configured to propagate the stimulation pattern at a different rate for different rows.

4. The haptic interface device of claim 1, wherein the controller is configured to present:
one of two partial units of information in the stimulation pattern at a same time;
a portion of a first character and a portion of a second character in the stimulation pattern at a same time; or
a portion of a first word and a portion of a second word in the stimulation pattern at a same time.

5. The haptic interface device of claim 1, wherein the controller is configured to move the array across the user's skin in order to propagate the stimulation pattern on the user's skin.

6. The haptic interface device of claim 1, wherein the array comprising the haptic stimulation elements comprises a ring of haptic stimulation elements, and wherein the controller is configured to rotate the ring across the user's skin in order to propagate the stimulation pattern on the user's skin.

7. The haptic interface device of claim 1, wherein the controller is configured to modify the stimulation pattern over time based on a long short-term memory model.

8. The haptic interface device of claim 1, wherein the controller is configured to spatially represent a first dimension and a second dimension of a three-dimensional object in the array and temporally represent a third dimension of the three-dimensional object in the array.

9. The haptic interface device of claim 8, wherein the controller is configured to control a rate at which the stimulation pattern propagates in different regions of the array in order to temporally represent the third dimension of the three-dimensional object.

10. The haptic interface device of claim 1, wherein the controller is configured to represent velocity of an object in the array comprising the haptic stimulation elements by a rate at which the stimulation pattern is propagated.

11. A method of providing a haptic stimulation interface, the method comprising:
generating a stimulation pattern with an array comprising haptic stimulation elements; and
continually propagating the stimulation pattern on a user's skin by repeatedly eliminating a portion of a first end of the stimulation pattern and replacing the portion eliminated with a new portion at a second end of the stimulation pattern.

12. The method of claim 11, further comprising moving the array comprising the haptic stimulation elements over the user's skin in order to propagate the stimulation pattern on the user's skin.

13. The method of claim 11, further comprising rotating the array comprising the haptic stimulation elements across the user's skin in order to propagate the stimulation pattern on the user's skin.

14. The method of claim 11, wherein continually propagating the stimulation pattern comprises:
spatially representing a first dimension and a second dimension of a three-dimensional object in the array; and
temporally representing a third dimension of the three-dimensional object in the array.

15. The method of claim 14, further comprising controlling a rate at which the stimulation pattern propagates in different regions of the array in order to temporally represent the third dimension of the three-dimensional object.

16. The method of claim 11, wherein continually propagating the stimulation pattern comprises representing velocity of an object in the array comprising the haptic stimulation elements by a rate at which the stimulation pattern is propagated.

17. A haptic stimulation device comprising:
a haptic stimulation interface comprising an array of tactile pixels configured to stimulate receptors in skin of a user with a stimulation pattern;
a receiver configured to receive information to present in the haptic stimulation interface; and
a processor configured to continually propagate the stimulation pattern on the skin of the user by eliminating a portion of a first end of the stimulation pattern and replacing the portion eliminated with a new portion at a second end of the stimulation pattern in order to present the information.

18. The haptic stimulation device of claim 17, wherein the processor is configured to propagate the stimulation pattern at a constant rate on the skin of the user.

19. The haptic stimulation device of claim 17, wherein the array comprises rows and columns of the tactile pixels, and wherein the processor is configured to propagate the stimulation pattern at a same rate for each row.

20. The haptic stimulation device of claim 17, wherein the array comprises rows and columns of the tactile pixels, and wherein the processor is configured to propagate the stimulation pattern at a different rate for different rows.

* * * * *

UNITED STATES PATENT AND TRADEMARK OFFICE
CERTIFICATE OF CORRECTION

| | | |
|---|---|---|
| PATENT NO. | : 11,715,356 B2 | Page 1 of 1 |
| APPLICATION NO. | : 17/511270 | |
| DATED | : August 1, 2023 | |
| INVENTOR(S) | : Fei Liu et al. | |

It is certified that error appears in the above-identified patent and that said Letters Patent is hereby corrected as shown below:

On the Title Page

Item (56) Foreign Patent Documents
Delete "FR 2882881 A1 8/2006"

Signed and Sealed this
Nineteenth Day of September, 2023

Katherine Kelly Vidal
*Director of the United States Patent and Trademark Office*